(12) United States Patent
Dunsmore et al.

(10) Patent No.: US 9,086,376 B1
(45) Date of Patent: Jul. 21, 2015

(54) AUTOMATIC FIXTURE REMOVAL USING ONE-PORT MEASUREMENT

(71) Applicant: Keysight Technologies, Inc., Minneapolis, MN (US)

(72) Inventors: Joel P. Dunsmore, Sebastopol, CA (US); Ning Cheng, Beijing (CN); Ya-Ping Zhang, Beijing (CN)

(73) Assignee: Keysight Technologies, Inc., Santa Rosa, CA (US)

( * ) Notice: Subject to any disclaimer, the term of this patent is extended or adjusted under 35 U.S.C. 154(b) by 2 days.

(21) Appl. No.: 14/156,401

(22) Filed: Jan. 15, 2014

(51) Int. Cl.
*G01N 21/47* (2006.01)

(52) U.S. Cl.
CPC ..................................... *G01N 21/47* (2013.01)

(58) Field of Classification Search
USPC .......... 356/445–448, 73.1, 335–343; 702/59, 702/76, 104, 106, 118, 189; 250/227.11; 385/12, 28, 37; 324/601, 617, 534
See application file for complete search history.

(56) References Cited

U.S. PATENT DOCUMENTS

| | | | |
|---|---|---|---|
| 5,592,282 A * | 1/1997 | Hartog | 356/44 |
| 7,157,918 B2 | 1/2007 | Adamian | |
| 7,170,297 B1 | 1/2007 | Dunsmore | |
| 2002/0057093 A1* | 5/2002 | Knox | 324/617 |
| 2002/0130667 A1* | 9/2002 | Noe | 324/534 |
| 2005/0110502 A1* | 5/2005 | Wang et al. | 324/601 |
| 2005/0234666 A1* | 10/2005 | Taylor et al. | 702/66 |
| 2015/0066408 A1* | 3/2015 | Armbrecht et al. | 702/64 |

OTHER PUBLICATIONS

Dunsmore, Handbook of Microwave Component Measurements with Advanced VNA Techniques, Wiley Print, 2012, p. 214, 229-241.
Dunsmore, et al. "Characterizations of asymmetric fixtures with a two-gate approach", Microwave Measurement Conference (ARFTG), Jun. 2011, p. 1-6.

* cited by examiner

*Primary Examiner* — Hoa Pham

(57) ABSTRACT

Scattering parameters of a test fixture having a first port and a second port are measured by providing a test instrument; outputting a one-port reflection test signal from the test instrument to the first port with the second port terminated in a reflective termination having a known reflection coefficient, and receiving at the test instrument a one-port reflection measurement signal from the first port; subjecting the one-port reflection measurement signal to first time gating to generate a first time-gated measurement signal, the first time gating using a first gating function temporally disposed about the first port; subjecting the one-port reflection measurement signal to second time gating to generate a second time-gated measurement signal, the second time gating using a second gating function temporally disposed about the termination; and deriving the scattering parameters from the first time-gated measurement signal and the second time-gated measurement signal.

20 Claims, 16 Drawing Sheets

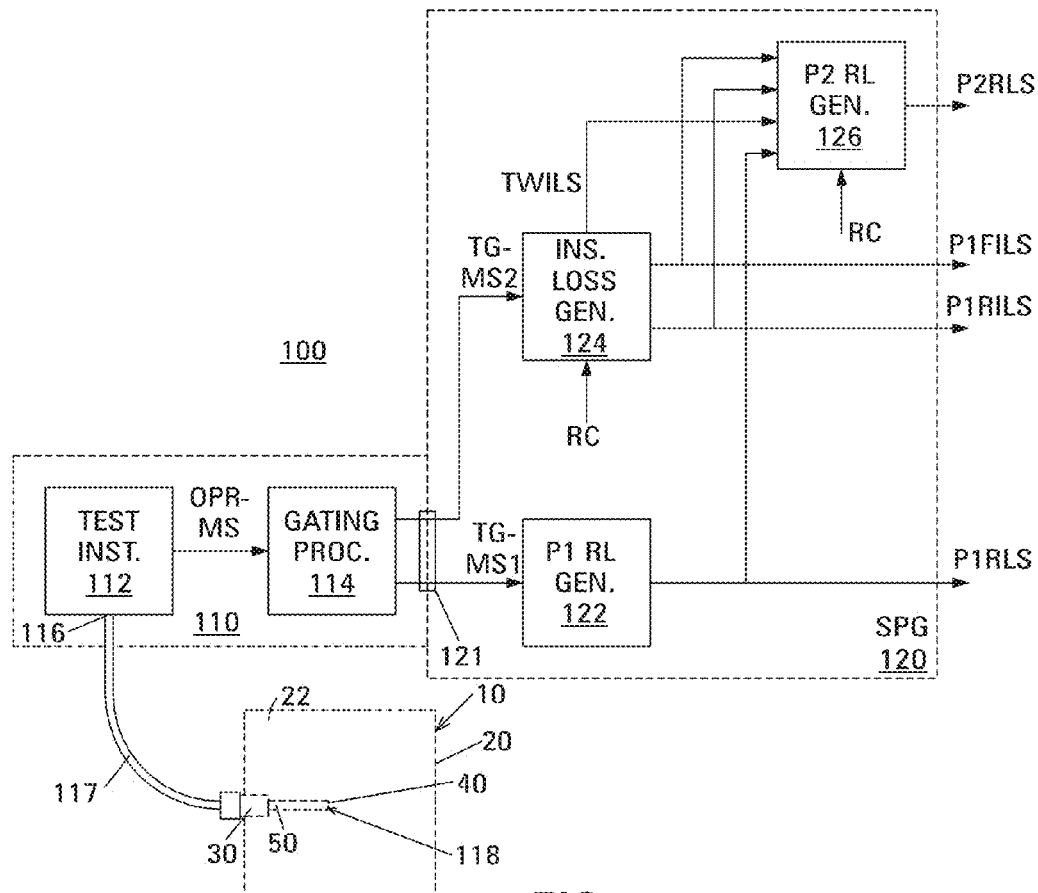

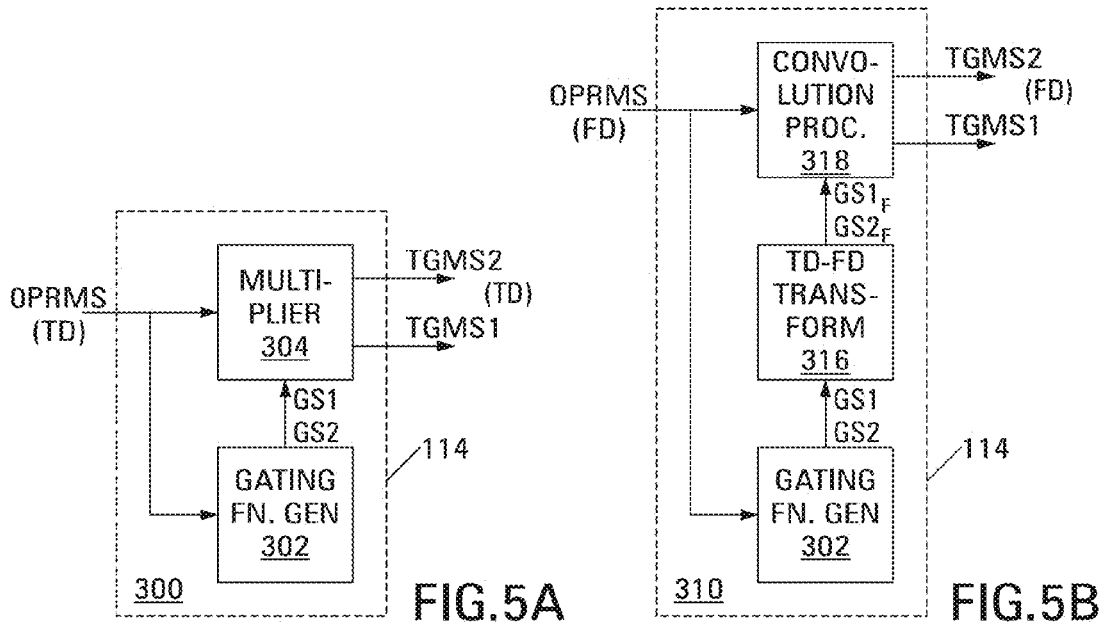
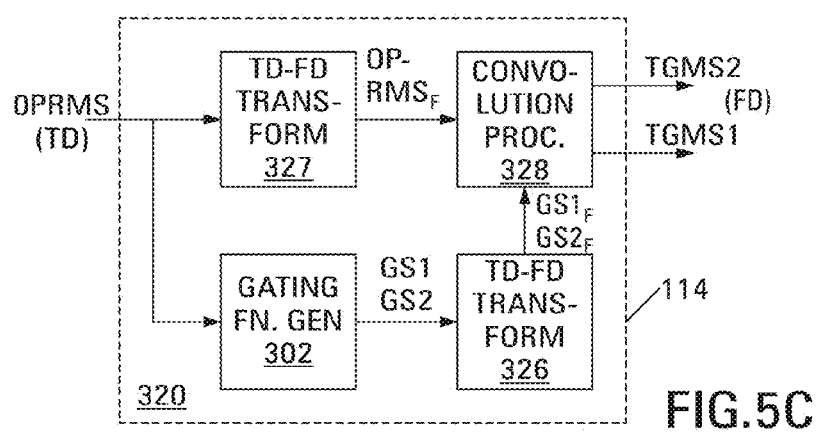
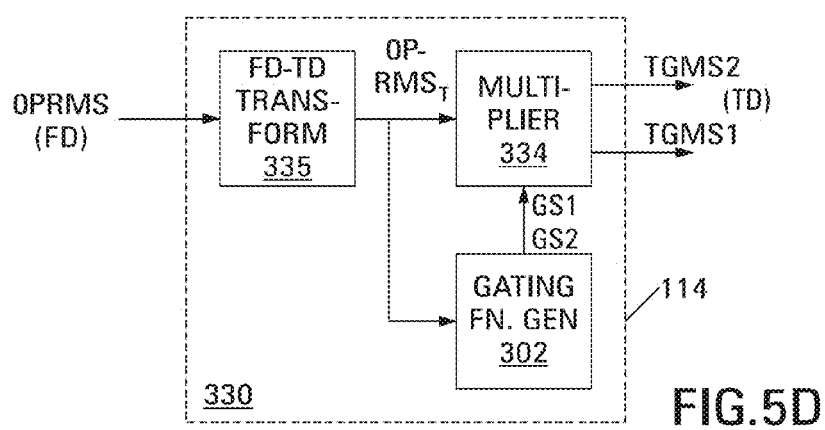

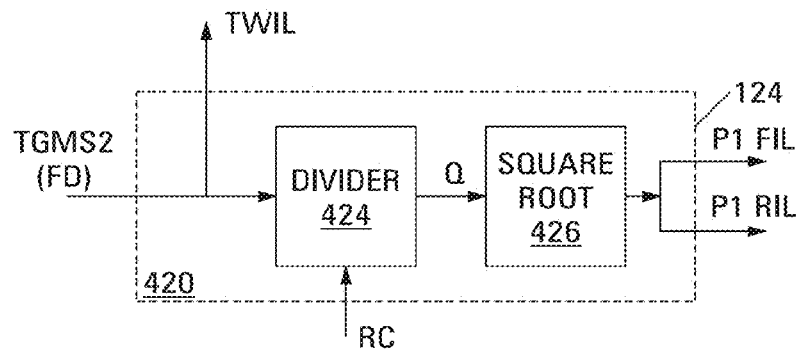
FIG.8A
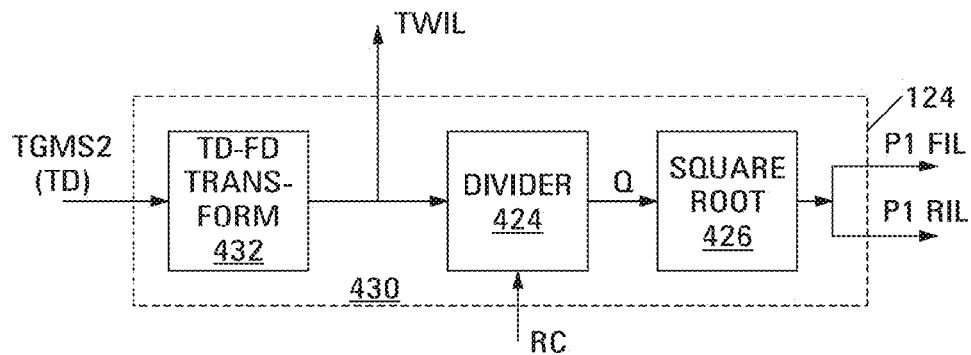
FIG.8B
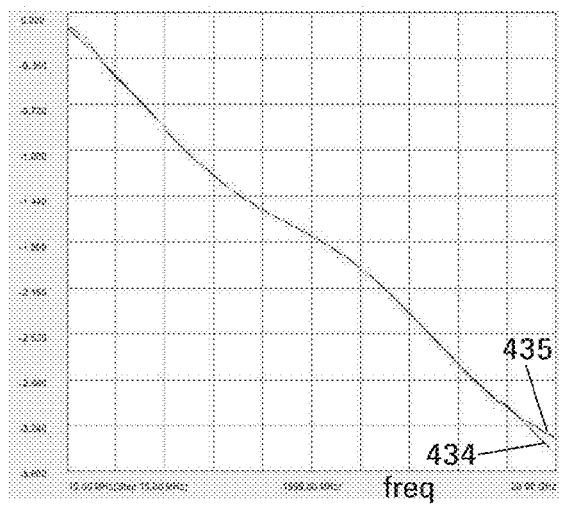 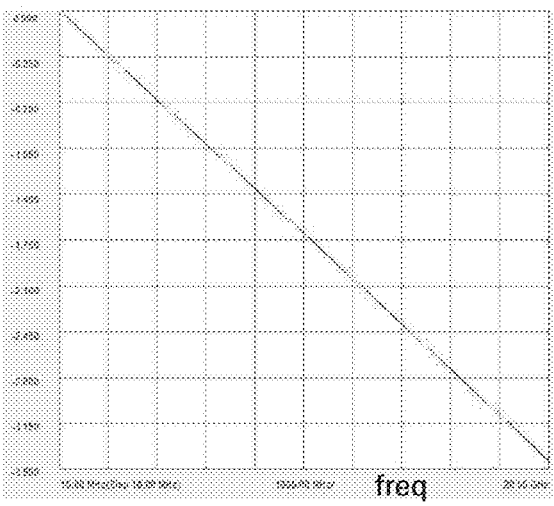
FIG.8C  FIG.8D

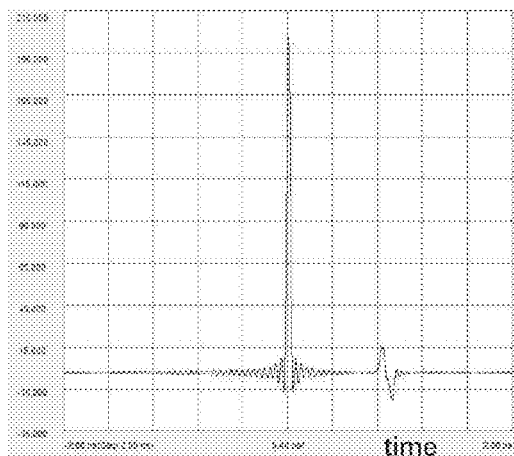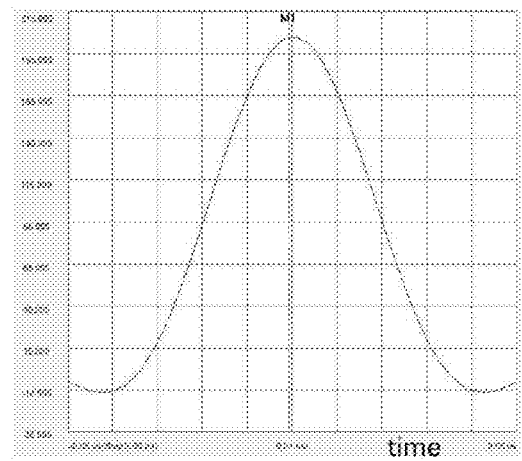
FIG.10A  FIG.10B
FIG.10C
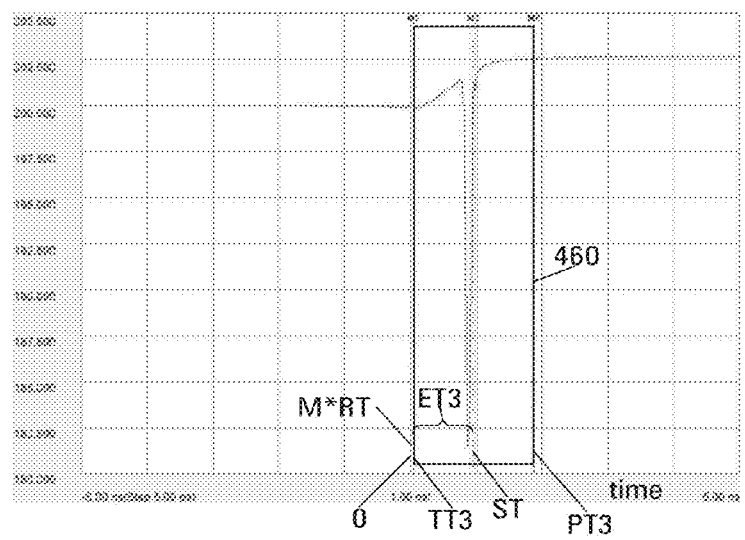
FIG.10D

```
┌─────────────────────────────────────────────────────────────┐
│  MULTIPLY THE ONE-PORT REFLECTION MEASUREMENT SIGNAL AND THE │
│  FIRST GATING FUNCTION SIGNAL TO GENERATE THE FIRST TIME-GATED│
│       MEASUREMENT SIGNAL AS A TIME-DOMAIN SIGNAL              │
│                          602                                  │
└─────────────────────────────────────────────────────────────┘
                            │  600
                            ▼
┌─────────────────────────────────────────────────────────────┐
│  MULTIPLY THE ONE-PORT REFLECTION MEASUREMENT SIGNAL AND THE │
│   SECOND TIME DOMAIN GATING FUNCTION SIGNAL TO GENERATE THE  │
│  SECOND TIME-GATED MEASUREMENT SIGNAL AS A TIME-DOMAIN SIGNAL│
│                          604                                  │
└─────────────────────────────────────────────────────────────┘
```

FIG.15A

```
┌─────────────────────────────────────────────────────────────┐
│    TRANSFORM THE FIRST GATING FUNCTION SIGNAL AND THE SECOND │
│   GATING FUNCTION SIGNAL FROM THE TIME DOMAIN TO THE FREQUENCY│
│   DOMAIN TO GENERATE A FREQUENCY-DOMAIN FIRST GATING FUNCTION│
│   SIGNAL AND A FREQUENCY-DOMAIN SECOND GATING FUNCTION SIGNAL,│
│                         RESPECTIVELY                          │
│                            612                                │
└─────────────────────────────────────────────────────────────┘
                            │  610
                            ▼
┌─────────────────────────────────────────────────────────────┐
│  SUBJECT THE FREQUENCY-DOMAIN FIRST GATING FUNCTION SIGNAL AND│
│  THE ONE-PORT REFLECTION MEASUREMENT SIGNAL TO CONVOLUTION TO │
│      GENERATE THE FIRST TIME-GATED MEASUREMENT SIGNAL AS      │
│                 A FREQUENCY-DOMAIN SIGNAL                     │
│                          614                                  │
└─────────────────────────────────────────────────────────────┘
                            │
                            ▼
┌─────────────────────────────────────────────────────────────┐
│   SUBJECT THE FREQUENCY-DOMAIN SECOND GATING FUNCTION SIGNAL │
│  AND THE ONE PORT REFLECTION MEASUREMENT SIGNAL TO CONVOLUTION│
│    TO GENERATE THE SECOND TIME-GATED MEASUREMENT SIGNAL AS    │
│                 A FREQUENCY-DOMAIN SIGNAL                     │
│                          616                                  │
└─────────────────────────────────────────────────────────────┘
```

FIG.15B

AUTOMATIC FIXTURE REMOVAL USING ONE-PORT MEASUREMENT

BACKGROUND

To measure the scattering parameters (S-parameters), such as S11, S12, S21 and S22, of a device under test (DUT) with a non-coaxial interface, the DUT is typically installed in a test fixture having a coaxial interface. Such test fixtures are not electrically transparent. Consequently, the test fixture must be characterized to determine its S-parameters so that the S-parameters of the test fixture can be de-embedded from the measurement results to determine the S-parameters of the DUT itself.

Determining the S-parameters of the test fixture with accuracy and repeatability sufficient not to impair the accuracy and repeatability of the S-parameters of the DUT has proved to be challenging in practice.

Accordingly, what is needed is a way to determine the S-parameters of a test fixture used to measure a device under test having a non-coaxial interface with an accuracy that does not impair the accuracy with which the S-parameters of the DUT can be determined.

BRIEF DESCRIPTION OF THE DRAWINGS

FIG. 1 is a block diagram showing an example of a test fixture characterization system as disclosed herein.

FIG. 2A is a graph showing an example of a one-port reflection measurement signal output by an example of a test instrument that operates in the time domain.

FIG. 2B is a graph showing an example of a one-port reflection measurement signal output by an example of a test instrument that operates in the frequency domain.

FIGS. 5A-5D are block diagrams showing simplified examples of a gating processor.

FIGS. 8A and 8B are block diagrams showing simplified examples of an insertion loss generator.

FIGS. 8C and 8D are graphs showing the variation with frequency of the logarithm of the magnitude and the phase, respectively, of the first port forward insertion loss S21 of an example of a test fixture.

FIGS. 10A and 10B are graphs showing the impulse response of an example of part of the second port return loss generator.

FIG. 10C is a graph showing an example of the impulse response of the second port return loss as determined by the second port return loss generator shown in FIG. 9B.

FIG. 10D is a graph showing the impulse response of an example of a preliminary second port return loss signal marked with an example of a third gating window that in part defines the third gating function.

FIGS. 15A-15D are flow charts showing examples of methods of applying time gating to time-domain and frequency-domain one-port reflection measurement signals.

DETAILED DESCRIPTION

Figure 3A:
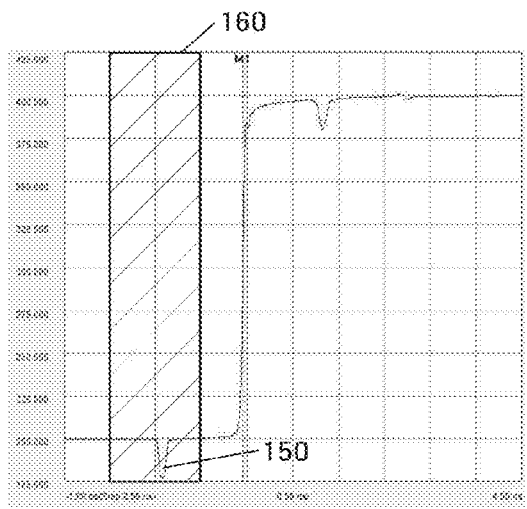
FIG. 3A is a graph showing an example of a first gating window that in part defines the first time gating to which the one-port reflection measurement signal is subject.

FIG. 1 is a block diagram showing an example 100 of a test fixture characterization system as disclosed herein. FIG. 1 shows test fixture characterization system 100 connected to an example 10 of a test fixture to which a device-under-test (DUT) having a non-coaxial interface can be connected. In the example shown, test fixture 10 includes a substrate 20 having an insulating surface 22. Test fixture 10 additionally includes a first port 30, a second port 40, and a strip line 50 extending over insulating surface 22 from first port 30 to second port 40. Substrate 20 additionally includes a ground plane (not shown) that covers at least part of the surface (not shown) of substrate 20 opposite insulating surface 22. When test fixture 10 is used to perform measurements on a DUT (not shown), the DUT is electrically connected to second port 40.

Test fixture 10 is not part of test fixture characterization system 100, but is the test fixture characterized by the test fixture characterization system. Test fixture characterization system 100 may also be used to characterize test fixtures having opposed pairs of ports but otherwise structured differently from the exemplary test fixture 10.

Test fixture characterization system 100 includes a test system 110 and a scattering parameter generator (SPG) 120. In the example shown, test system 110 includes a test instrument 112 and a gating processor 114. In other examples, test instrument 112 includes a built-in gating processor. Test instrument 112 includes a test port 116 connected by a test cable 117 to the first port 30 of test fixture 10.

The second port 40 of test fixture 10 is terminated in a reflective termination, shown schematically at 118, having a known reflection coefficient F. In an example, reflective termination 118 is an open circuit termination or a short circuit termination. An open-circuit termination may be provided by leaving second port 40 unconnected. Second port 40 with nothing connected to it will be regarded as being terminated in a reflective termination having a known reflection coefficient. A short-circuit termination may be provided by connecting second port 40 directly to ground plane 24. In another example, a termination having a characteristic impedance different from the characteristic impedance of strip line 50 is connected between second port 40 and ground plane 24 to provide reflective termination 118. For example, a termination having a characteristic impedance of 75Ω is connected between second port 40 and ground plane 24 in an example in which strip line 50 has a characteristic impedance of 50Ω. The reflection coefficient of an uncalibrated termination may be known or may be measured using test instrument 112 or another suitable test instrument, for example, a vector network analyzer (VNA).

Test system 110 performs a one-port reflection measurement on the first port 30 of test fixture 10 to generate a one-port reflection measurement signal OPRMS, and subjects one-port reflection measurement signal OPRMS to time gating, including a first time gating and a second time gating, different from the first time gating, to generate a first time-gated measurement signal TGMS1 and a second time-gated measurement signal TGMS2. Test system 110 outputs the time-gated measurement signals to scattering parameter generator 120. Scattering parameter generator 120 derives from the time-gated measurement signals a set of scattering parameters that characterize test fixture 10. In the example shown, the first port 30 and the second port 40 of test fixture 10 are single-ended ports, and scattering parameter generator 120 derives scattering parameters first port return loss S11, first port reverse insertion loss S12, first port forward insertion loss S21 and second port return loss S22 for the test fixture. In another example (not shown), the first port and the second port of the test fixture are differential ports, and scattering parameter generator 120 derives differential scattering parameters first port return loss Sdd11, first port reverse insertion loss Sdd12, first port forward insertion loss Sdd21 and second port return loss Sdd22 and common-mode scattering parameters first port return loss Scc11, first port reverse insertion loss Scc12, first port forward insertion loss Scc21, and second port return loss Scc22 for test fixture 10.

In the example shown, scattering parameter generator 120 includes an input 121, a first port return loss generator 122, an insertion loss generator 124, and a second port return loss generator 126. Scattering parameter generator 120 receives first time-gated measurement signal TGMS1 and second time-gated measurement signal TGMS2 at input 121. First port return loss generator 122 derives a first port return loss signal P1RLS from the first time-gated measurement signal TGMS1. First port return loss signal P1RLS represents the return loss at the first port 30 of test fixture 10. Insertion loss generator 124 derives a two-way insertion loss signal TWILS, a first port reverse insertion loss signal P1RILS, and a first port forward insertion loss signal P1FILS from second time-gated measurement signal TGMS2 and the reflection coefficient of reflective termination 118. Two-way insertion loss signal TWILS, first port reverse insertion loss signal P1RILS, and first port forward insertion loss signal P1FILS represent the two-way insertion loss, the reverse insertion loss, and the forward insertion loss, respectively, of the first port 30 of test fixture 10. Second port return loss generator 126 derives a second port return loss signal P2RLS from the first port return loss signal, the two-way insertion loss signal, the first port reverse insertion loss signal, the first port forward insertion loss signal, and the reflection coefficient of reflective termination 118. Second port return loss signal P2RLS represents the return loss of the second port 40 of test fixture 10

In test system 110, test instrument 112 subjects test fixture 10 to a one-port reflection measurement and outputs (or internally of transfers) a one-port reflection measurement signal OPRMS to gating processor 114. In an example, a time-domain reflectometer or another type of test instrument that determines impulse responses in the time domain is used as test instrument 112. An example of a suitable instrument that may be used as test instrument 112 is a model 86100C DCA-J-TDR/TDT oscilloscope sold by Agilent Technologies, Inc., Santa Clara, Calif. In another example, a vector network analyzer or another type of test instrument that determines spectral responses in the frequency domain is used as test instrument 112. Another example of a suitable instrument that may be used as test instrument 112 is a model N5242A network analyzer sold by Agilent Technologies, Inc., Santa Clara, Calif.

Test instrument 112 outputs a one-port reflection test signal to the first port 30 of test fixture 10 via test port 116 and test cable 117. In an example in which test instrument 112 operates in the time domain, the one-port reflection test signal includes an amplitude pulse or a step. The amplitude pulse or step has a rise time short enough to include frequencies that cover the frequency range of interest over which the characteristics of test fixture 10 are to be measured. In an example in which test instrument 112 operates in the frequency domain, the one-port reflection test signal is a sine wave, square wave, or another suitable waveform whose frequency is swept over a frequency range of interest. The second port 40 of test fixture 10 reflects the one-port reflection test signal back to test instrument 112 as a one-port reflection measurement signal. Test instrument 112 receives the one-port reflection measurement signal via test cable 117 and test port 116, and outputs the one-port reflection measurement signal as one-port reflection measurement signal OPRMS. One-port reflection measurement signal OPRMS is a set of data representing the reflection of the one-port reflection test signal at the second port 40 of test fixture 10. In an example in which test instrument 112 operates in the time domain, the data set represents the impulse response of the reflected signal, i.e., the variation of amplitude of the one-port reflection measurement signal with time. The data set is generated at a sampling rate sufficiently high to capture the highest frequency in the frequency range of interest. In an example in which test instrument 112 operates in the frequency domain, the data set represents the spectrum of the one-port reflection measurement signal, i.e., the variation of amplitude of the one-port reflection measurement signal with frequency.

FIG. 2A is a graph showing an example of one-port reflection measurement signal OPRMS output by an example of test instrument 112 that operates in the time domain. FIG. 2B is a graph showing an example of one-port reflection measurement signal OPRMS output by an example of test instrument 112 that operates in the frequency domain. The example of one-port reflection measurement signal OPRMS shown in FIG. 2A is generated by an example of test fixture 10 in which the second port 40 of test fixture 10 is terminated with an open circuit. Test fixture 10 generates the example of one-port reflection measurement signal OPRMS shown in response to a one-port reflection test signal whose amplitude increases stepwise by about 200 mV. A slight mismatch between the characteristic impedance of test cable 117 and the first port 30 of test fixture 10 causes one-port reflection measurement signal OPRMS to exhibit an amplitude dip 150, where the amplitude of the signal momentarily falls and then recovers to its original level. Amplitude dip 150 indicates the temporal location of first port 30. Shortly thereafter, one-port reflection measurement signal OPRMS exhibits an amplitude step 152, where the amplitude of the signal increases sharply due to reflection of the one-port reflection test signal at the open-circuit termination at second port 40. The reflection causes the amplitude of one-port reflection measurement signal OPRMS to increase to approximately twice its original amplitude. Amplitude step 152 indicates the temporal location of second port 40. Thereafter, the mismatch at the first port 30 causes one-port reflection measurement signal OPRMS to exhibit a second amplitude dip 154, where the amplitude of the signal momentarily falls and then recovers to its original level.

Figure 3B:
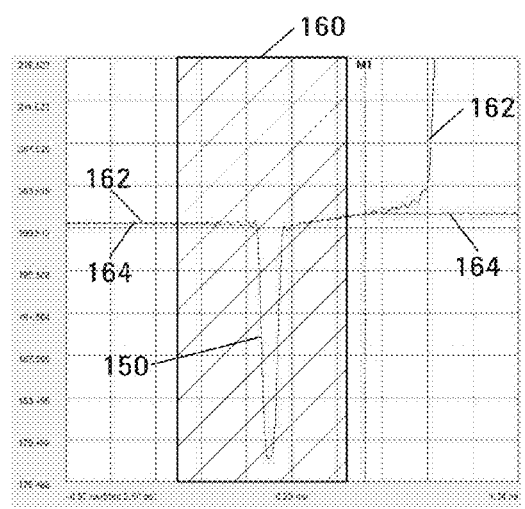
FIG. 3B is a graph showing an enlarged view of a portion of the one-port reflection measurement signal before and after it is subject to the first time gating.

To determine the scattering parameters that characterize test fixture 10, test system 110 subjects one-port reflection measurement signal OPRMS to time gating, including first time gating and second time gating, different from the first time gating. The first time gating and the second time gating extract respective portions of interest of the one-port reflection measurement signal. FIG. 3A is a graph showing an example of a first gating window 160 that in part defines the first time gating to which gating processor 114 subjects one-port reflection measurement signal OPRMS. In the example shown, one-port reflection measurement signal OPRMS is generated by an example of test instrument 112 that operates in the time domain. The first time gating is defined by a first time gating function GF1 and extracts a portion of measurement signal OPRMS disposed about amplitude dip 150. FIG. 3B is an enlarged view showing a portion of one-port reflection measurement signal OPRMS before (at 162) and after (at 164) it is subject to the first time gating.

Figure 4A:
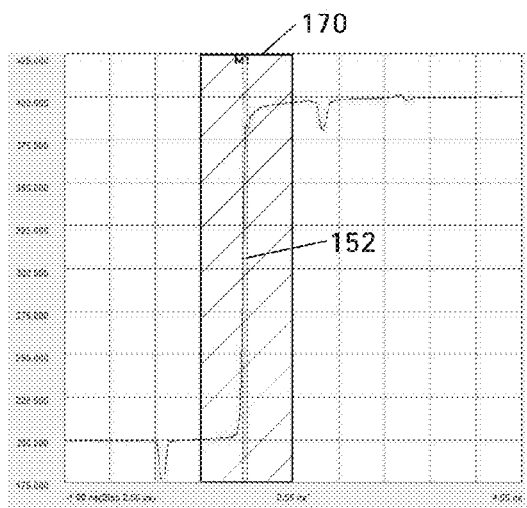
FIG. 4A is a graph showing an example of a second gating window that in part defines the second time gating to which the one-port reflection measurement signal is subject.
Figure 4B:
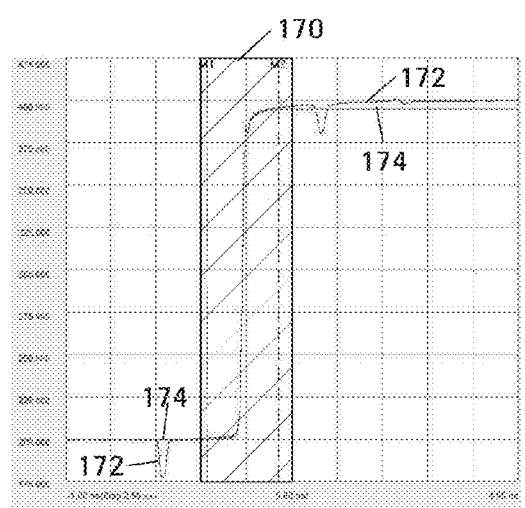
FIG. 4B is a graph showing a portion of the one-port reflection measurement signal before and after it is subject to the second time gating.

FIG. 4A is a graph showing an example of a second gating window 170 that in part defines the second time gating to which gating processor 114 subjects one-port reflection measurement signal OPRMS. In the example shown, one-port reflection measurement signal OPRMS is generated by an example of test instrument 112 that operates in the time domain. The second time gating is defined by a second time gating function GF2 and extracts a portion of the measurement signal disposed about amplitude step 152. FIG. 4B is a graph showing a portion of the one-port reflection measurement signal before (at 172) and after (at 174) it is subject to the second time gating.

In an example, each of first time gating function GF1 and second time gating function GF2 has a rectangular gating characteristic. The amplitude of portions of one-port reflection measurement signal OPRMS outside the gating window that defines the gating function is set to zero whereas the amplitude of the portion of the measurement signal within the gating window remains unchanged. Gating characteristics other than a rectangular gating characteristic may also be used. The examples shown in FIGS. 3B and 4B were obtained using respective gating functions having a Kaiser-Bessel gating characteristic that produces less ripple than a rectangular gating characteristic.

Gating processor 114 receives one-port reflection measurement signal OPRMS from test instrument 112. The gating processor first examines measurement signal OPRMS to identify the respective portions of the measurement signal that exhibit amplitude dip 150 and amplitude step 152. Gating processor 114 is additionally supplied with information defining the temporal width of the first gating window nominally centered on amplitude dip 150 and the temporal width of the second gating window nominally centered on amplitude step 152. Gating processor 114 generates first gating function GF1 from the temporal location of amplitude dip 150, the information defining the temporal width of the first gating window, and the specified gating characteristic, and generates second gating function GF2 from the temporal location of amplitude step 152, the information defining the temporal width of the second gating window, and the specified gating characteristic. Alternatively, information defining a respective start time and stop time of the first gating window and the second gating window may be used to define the respective gating window. Gating processor 114 then subjects one-port reflection measurement system OPRMS to time gating defined by first gating function GF1 to generate first time-gated measurement signal TGMS1, and subjects one-port reflection measurement signal OPRMS to time gating defined by second gating function GF2 to generate second time-gated measurement signal TGMS2. Gating processor 114 (and test system 110) output first time-gated measurement signal TGMS1 and second time-gated measurement signal TGMS2 to the input 121 of scattering parameter generator 120.

First time-gated measurement signal TGMS1 is a portion of one-port reflection measurement signal OPRMS temporally disposed about the first port 30 of test fixture 10 and second time-gated measurement TDM2 is a portion of one-port reflection measurement signal OPRMS temporally disposed about the second port 40 of test fixture 10. As will be described in greater detail below with reference to FIGS. 5A-5D, some embodiments of gating processor 114 apply time gating to one-port reflection measurement signal OPRMS in the time domain, whereas other embodiments of gating processor 114 apply the time gating in the frequency domain.

FIGS. 5A-5D are block diagrams showing simplified examples of gating processor 114. The examples shown in FIGS. 5A-5D are simplified in the sense that buffers that temporarily store the signals processed by and generated by the various elements of the gating processors are omitted to simplify the drawings and the descriptions thereof.

FIG. 5A shows an example 300 of gating processor 114 suitable for use in an embodiment of characterization system 100 in which test instrument 112 generates one-port reflection measurement signal OPRMS as a time-domain signal, and scattering parameter generator 120 is configured to receive time-domain signals as time-gated measurement signals TGMS1, TGMS2.

Gating processor 300 includes a gating function generator 302 and a multiplier 304. Gating processor 300 receives a time-domain one-port reflection measurement signal OPRMS from test instrument 112.

In gating processor 300, gating function generator 302 examines time-domain one-port reflection measurement signal OPRMS to determine the temporal positions of the first port 30 and the second port 40 of test fixture 10, and generates a first gating function signal GS1 that represents the first time gating function GF1, and additionally generates a second gating function signal GS2 that represents the second time grating function GF2 as time-domain signals. An example of a gating function generator that may be used as gating function generator 302 will be described below with reference to FIGS. 6A-6C.

Multiplier 304 receives first gating function signal GS1 representing first gating function GF1 from gating function generator 302 and time-domain one-port reflection measurement signal OPRMS from test instrument 112. Multiplier 304 multiplies time-domain one-port reflection measurement signal OPRMS and first gating function signal GS1 to generate first time-gated measurement signal TGMS1 as a time-domain signal. Multiplier 304 additionally receives second gating function signal GS2 representing second gating function GF2 from gating function generator 302, and multiplies time-domain one-port reflection measurement signal OPRMS and second gating function signal GS2 to generate second time-gated measurement signal TGMS2 as a time-domain signal. Gating processor 300 outputs time-domain time-gated measurement signals TGMS1 and TGMS2 to scattering parameter generator 120.

FIG. 5B shows an example 310 of gating processor 114 suitable for use in an embodiment of characterization system 100 in which test instrument 112 generates one-port reflection measurement signal OPRMS as a frequency-domain signal, and scattering parameter generator 120 is configured to receive frequency-domain signals as time-gated measurement signals TGMS1, TGMS2.

Gating processor 310 includes above-described gating function generator 302, a time domain to frequency domain transform processor 316 and a convolution processor 318. Gating processor 310 receives a frequency-domain one-port reflection measurement signal from test instrument 112. Gating function generator 302 receives frequency-domain one-port reflection measurement signal OPRMS in response to which it generates first gating function signal GS1 and second gating function signal GS2.

Time domain to frequency domain transform processor 316 receives first gating function signal GS1 from gating function generator 302 and transforms the first gating function signal from the time domain to the frequency domain to generate a frequency-domain first gating function signal $GS1_F$. Transform processor 316 additionally receives second gating function signal GF2 from gating function generator 302 and transforms the second gating function signal from the time domain to the frequency domain to generate a frequency-domain second gating function signal $GS2_F$.

Convolution processor 318 receives frequency-domain first gating function signal $GS1_F$ from transform processor 316, and receives frequency-domain one-port reflection measurement signal OPRMS from test instrument 112. Convolution processor 318 subjects frequency-domain one-port reflection measurement signal OPRMS and frequency-domain first gating function signal $GS1_F$ to convolution processing to generate first time-gated measurement signal TGMS1 as a frequency-domain signal. Convolution processor 318 additionally receives frequency-domain second gating function signal $GS2_F$ from transform processor 316, and subjects frequency-domain one-port reflection measurement signal OPRMS and frequency-domain second gating function signal $GS2_F$ to convolution processing to generate second time-gated measurement signal TGMS2 as a frequency-domain signal. Gating processor 310 outputs frequency-domain time-gated measurement signals TGMS1 and TGMS2 to scattering parameter generator 120.

FIG. 5C shows an example 320 of gating processor 114 suitable for use in an embodiment of characterization system 100 in which test instrument 112 generates one-port reflection measurement signal OPRMS as a time-domain signal, and scattering parameter generator 120 is configured to receive frequency-domain signals as time-gated measurement signals TGMS1, TGMS2.

Gating processor 320 includes above-described gating function generator 302, a first time domain to frequency domain transform processor 326, a second time domain to frequency domain transform processor 327, and a convolution processor 328. Gating processor 320 receives a time-domain one-port reflection measurement signal OPRMS from test instrument 112. Gating function generator 302 receives time-domain one-port reflection measurement signal OPRMS in response to which it generates first gating function signal GS1 and second gating function signal GS2.

First time domain to frequency domain transform processor 326 receives first gating function signal GS1 from gating function generator 302 and transforms the first gating function signal from the time domain to the frequency domain to generate a frequency-domain first gating function signal $GS1_F$. First time domain to frequency domain transform processor 326 additionally receives second gating function signal GS2 from gating function generator 302 and transforms the second gating function signal from the time domain to the frequency domain to generate a frequency-domain second gating function signal $GS2_F$.

Second time domain to frequency domain transform processor 327 receives time-domain one-port reflection measurement signal OPRMS from test instrument 112 and transforms the one-port reflection measurement signal from the time domain to the frequency domain to generate a frequency-domain one-port reflection measurement signal $OPRMS_F$.

Convolution processor 328 receives frequency-domain first gating function signal $GS1_F$ from first time domain to frequency domain transform processor 326, and receives frequency-domain one-port reflection measurement signal $OPRMS_F$ from second time domain to frequency domain transform processor 327. Convolution processor 328 subjects frequency-domain one-port reflection measurement signal $OPRMS_F$ and frequency-domain first gating function signal $GS1_F$ to convolution processing to generate a first time-gated measurement signal $TGMS1_F$ as a frequency-domain signal. Convolution processor 328 additionally receives frequency-domain second gating function signal $GS2_F$ from first time domain to frequency domain transform processor 326, and subjects frequency-domain one-port reflection measurement signal $OPRMS_F$ and frequency-domain second gating function signal $GS2_F$ to convolution processing to generate second time-gated measurement signal $TGMS2_F$ as a frequency-domain signal. Gating processor 320 outputs frequency-domain time-gated measurement signals TGMS1 and TGMS2 to scattering parameter generator 120.

Another example (not shown) of gating processor 114 suitable for use in an embodiment of characterization system 100 in which test instrument 112 generates one-port reflection measurement signal OPRMS in the time domain, and scattering parameter generator 120 is configured to receive frequency-domain signals as time-gated measurement signals TGMS1, TGMS2 is based on gating processor 300 shown in FIG. 5A. Added to gating processor 300 is a time domain to frequency domain transform processor (not shown) connected to receive the time-domain time-gated measurement signals TGMS1 and TGMS2 generated by multiplier 304. The added time domain to frequency domain transform processor transforms time-gated measurement signals TGMS1, TGMS2 from the time domain to the frequency domain.

FIG. 5D shows an example 330 of a gating processor suitable for use in an embodiment of characterization system 100 in which test instrument 112 generates one-port reflection measurement signal OPRMS as a frequency-domain signal, and scattering parameter generator 120 is configured to receive time-domain signals as time-gated measurement signals TGMS1, TGMS2.

Gating processor 330 includes above-described gating function generator 302, a multiplier 334, and a frequency domain to time domain transform processor 335. Gating processor 330 receives a frequency-domain one-port reflection measurement signal OPRMS from test instrument 112.

Frequency domain to time domain transform processor 335 receives frequency-domain one-port reflection measurement signal OPRMS and transforms the one-port reflection measurement signal from the frequency domain to the time domain to generate a time-domain one-port reflection measurement signal $OPRMS_T$. Gating function generator 302 receives time-domain one-port-port reflection measurement signal from frequency domain to time domain transform processor 335. Gating function generator 302 generates first gating function signal GS1 and second gating function signal GS2 in response to time-domain one-port reflection measurement signal $OPRMS_T$.

Multiplier 334 receives time-domain first gating function signal GS1 from gating function generator 302 and time-domain one-port reflection measurement signal $OPRMS_T$ from transform processor 335. Multiplier 334 multiplies the time-domain one-port reflection measurement signal and the time-domain first gating function signal to generate first time-gated measurement signal TGMS1 as a time-domain signal. Multiplier 334 additionally receives time-domain second gating function signal GS2 from gating function generator 302 and time-domain one-port reflection measurement signal $OPRMS_T$ from transform processor 335. Multiplier 334 multiplies the time-domain one-port reflection measurement signal and the time-domain second gating function signal to generate second time-gated measurement signal TGMS2 as a time-domain signal. Gating processor 330 outputs time-domain time-gated measurement signals TGMS1 and TGMS2 to scattering parameter generator 120.

In some examples of gating processors 300, 310, 320, 330, the gating processor generates frequency-domain time-gated measurement signals TGMS1 and TGMS2 sequentially. In other examples, the gating processor generates frequency-domain time-gated measurement signals TGMS1 and TGMS2 simultaneously.

The examples of gating processors 300, 310, 320, 330 shown in FIGS. 5A-5D output time-gated measurement signals TGMS1 and TGMS2 on respective conductors. In other examples (not shown), the gating processors output time-gated measurement signals TGMS1 and TGMS2 sequentially on a common conductor.

Figure 6A:
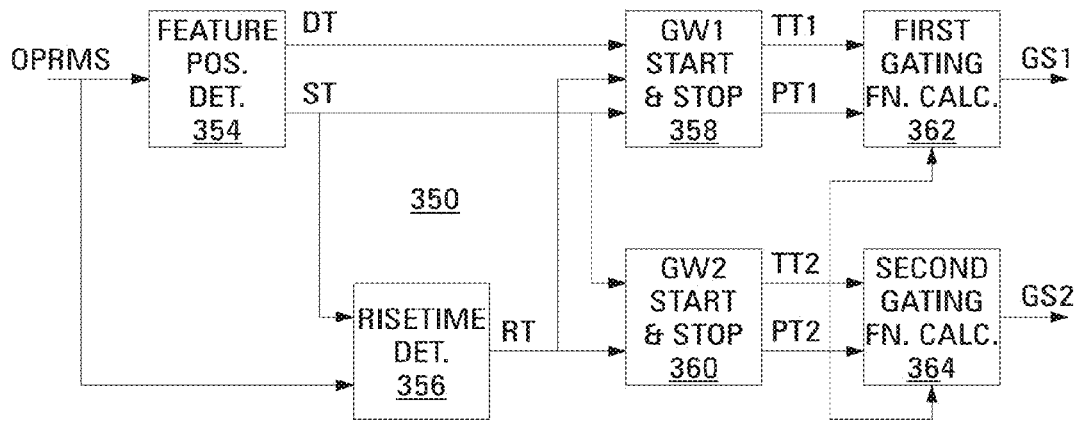
FIG. 6A is a block diagram showing an example of a gating function generator.

FIG. 6A is a block diagram showing an example 350 of a gating function generator suitable for use as gating function generator 302 in gating processors 300, 310, 320, 330. Gating function generator 350 includes a feature position detector 354, and rise time detector 356, a first gating window (GW1) start and stop time calculator 358, a second gating window (GW2) start and stop time calculator 360, a first gating function calculator 362, and a second gating function calculator 364. Gating function generator 350 receives one-port reflection measurement signal OPRMS from test instrument 112 (FIG. 1). Within gating function generator 350, one-port reflection measurement signal OPRMS is distributed to feature position detector 354 and rise time detector 356. In embodiments in which test instrument 112 generates one-port reflection measurement signal OPRMS as a frequency-domain signal, gating function generator 350 additionally includes a frequency domain to time domain transform processor (not shown) to convert measurement signal OPRMS from the frequency domain to the time domain. Other examples (not shown) of gating function generator 302 operate in the frequency domain and do not require conversion of a frequency-domain one-port reflection measurement signal to the time domain.

In gating function generator 350, feature position detector 354 examines one-port reflection measurement signal OPRMS to identify the temporal position of amplitude dip 150 and the temporal position of amplitude step 152 (FIG. 2A), and outputs a dip time DT indicating the temporal position of the amplitude dip in the reflection measurement signal, and a step time ST indicating the temporal position of the amplitude step in the reflection measurement signal.

Rise time detector 356 receives reflection measurement signal OPRMS and additionally receives step time ST from feature position detector 354. In response to step time ST, indicating the temporal position of amplitude step 152, rise time detector 356 determines the rise time RT of amplitude step 152. In an example, rise time detector 356 determines the change in the amplitude of measurement signal OPRMS at step time ST, and then determines the time taken for the amplitude of the measurement signal OPRMS to increase from 10% of the amplitude change to 90% of the amplitude change, or to change between other suitable percentages of the amplitude change, as rise time RT of amplitude step 152. Rise time detector 356 outputs rise time RT to first gating window start and stop time calculator 358 and to second gating window start and stop time calculator 360.

Figure 6B:
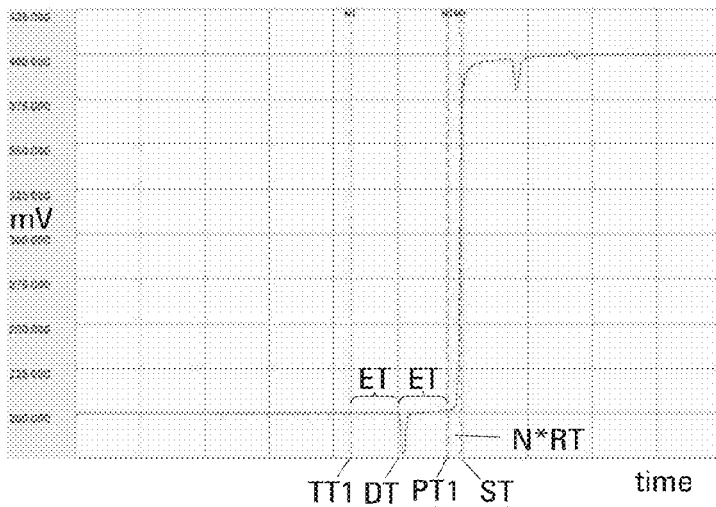
FIGS. 6B and 6C are graphs illustrating the calculation of the first gating window and the second gating window, respectively.

Referring additionally to FIG. 6B, first gating window start and stop time calculator 358 receives dip time DT and step time ST from feature position detector 354, and additionally receives rise time RT from rise time detector 356. First gating window start and stop time calculator 358 multiplies rise time RT by a multiplier N to generate a product and subtracts the product from step time ST to calculate the stop time PT1 of the first gating window. In an example, multiplier N is 10. In other examples, multiplier N is an integer or non-integer greater than or less than 10, depending on the length of strip line 50. Setting stop time PT1 at an elapsed time equal to N times, e.g., 10 times, the rise time of amplitude step 152 prior to the amplitude step creates the first gating window in a way that effectively excludes amplitude step 152. First gating window start and stop time calculator 358 additionally subtracts dip time DT from stop time PT1 to calculate an elapsed time. First gating window start and stop time calculator 358 then subtracts elapsed time ET from dip time DT to calculate the start time TT1 of the first gating window.

Figure 6C:
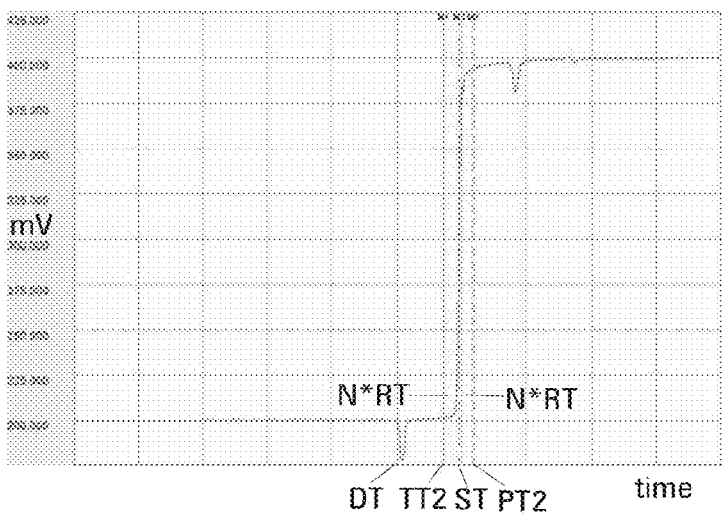

Referring additionally to FIG. 6C, second gating window start and stop time calculator 360 receives step time ST from feature position detector 354, and additionally receives rise time RT from rise time detector 356. Second gating window start and stop time calculator 360 multiplies rise time RT by above-described multiplier N to generate a product and subtracts the product from step time ST to calculate the start time TT2 of the second gating window. Alternatively, second gating window start and stop time calculator 360 reuses stop time PT1 calculated by first gating window start and stop time calculator 358 as start time TT2. Second gating window start and stop time calculator 360 then adds the above-describe product to step time ST to calculate the stop time PT2 of the second gating window. Setting start time TT2 and stop time PT2 at elapsed times ET equal to N times, e.g., 10 times, the rise time of amplitude step 152 before and after, respectively, step time ST creates the second gating window in a way that effectively includes all of amplitude step 152 within the second gating window.

First gating function start and stop time calculator 358 outputs the start time TT1 and the stop time PT1 of the first gating window to first gating function calculator 362. The first gating function calculator additionally receives a gating characteristic GC that defines the gating characteristics of the first and second gating functions. In other embodiments (not shown), gating characteristic GC is built in to first gating function calculator 362. In an example, gating characteristic GC is a rectangular gating characteristic. In another example, gating characteristic GC is a Kaiser-Bessel gating characteristic. In response to the start time TT1 and the stop time PT1 of the first gating window, and to gating characteristic GC, first gating function calculator 362 calculates first gating function GF1 that defines the first time gating and outputs first gating function signal GS1 that represents first gating function GF1.

Second gating function start and stop time calculator 360 outputs the start time TT2 and the stop time PT2 of the second gating window to second gating function calculator 364. The second gating function calculator additionally receives gating characteristic GC. In other embodiments (not shown), gating characteristic GC is built in to second gating function calculator 364. In response to the start time TT2 and the stop time PT2 of the second gating window, and to gating characteristic GC, second gating function calculator 364 calculates gating function GF2 that defines the second time gating, and outputs second gating function signal GS2 that represents second gating function GF2. In another example (not shown), second gating function calculator 364 uses a gating characteristic different from gating characteristic GC used by first gating function calculator 362.

Scattering parameter generator 120 (FIG. 1) will now be described in greater detail with reference to FIGS. 7A-7D, 8A-8D, 9A-9D, 10A-10D and 11A-11D. The examples shown in FIGS. 7A, 7B, 8A, 8B, 9A, 9B, 11A and 11B are simplified in the sense that buffers that temporarily store the signals processed by and generated by various elements of the scattering parameter generators shown therein are omitted to simplify the drawings and the descriptions thereof.

Figure 7A:
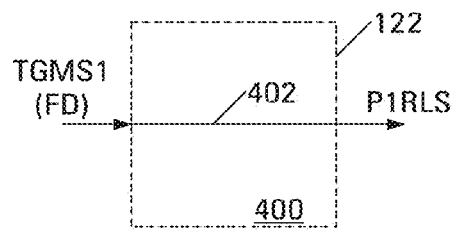
FIGS. 7A and 7B are block diagrams showing examples of a first port return loss generator.
Figure 7B:
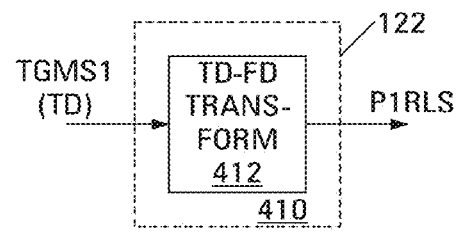

FIGS. 7A and 7B are block diagrams showing simplified examples of first port return loss generator 122. FIG. 7A is a block diagram showing an example 400 of a first port return loss generator suitable for use in an embodiment of characterization system 100 in which test system 110 generates first time-gated measurement signal TGMS1 as a frequency-domain signal. First port return loss generator 400 includes a conductor 402 connected between the input and output of first port return loss generator 400. First port return loss generator 400 receives first time-gated measurement signal TGMS1. First port return loss generator 400 outputs the first time-gated measurement signal via conductor 402 as a first port return loss signal P1RLS that represents the return loss of the first port 30 of test fixture 10 in the frequency domain.

FIG. 7B is a block diagram showing an example 410 of a first port return loss generator suitable for use in an embodiment of characterization system 100 in which test system 110 generates first time-gated measurement signal TGMS1 as a time-domain signal. First port return loss generator 410 includes a time domain to frequency domain transform processor 412. First port return loss generator 410 receives first time-gated measurement signal TGMS1. Time domain to frequency domain transform processor 412 transforms the first time-gated measurement signal from the time domain to the frequency domain to generate a frequency-domain first time-gated measurement signal. First port return loss generator 410 outputs the frequency-domain first time-gated measurement signal as first port return loss signal P1RLS that represents the return loss of the first port 30 of test fixture 10 in the frequency domain.

In an example in which the first port 30 of test fixture 10 is single ended, first port return loss signal P1RLS generated by first port return loss generator 400 or first port return loss generator 410 represents scattering parameter S11_fix of test fixture 10.

Figure 7C:
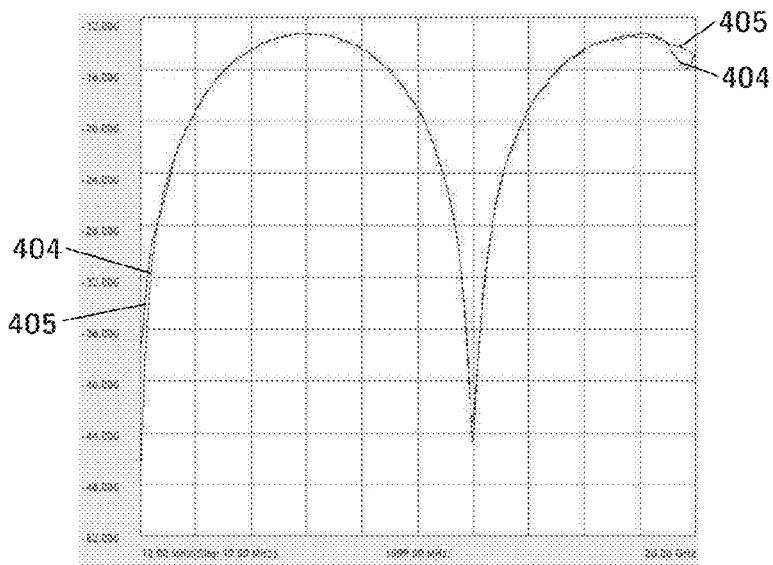
FIGS. 7C and 7D are graphs showing the variation with frequency of the logarithm of the magnitude and the phase, respectively, of the first port return loss S11 of an example of a test fixture.
Figure 7D:
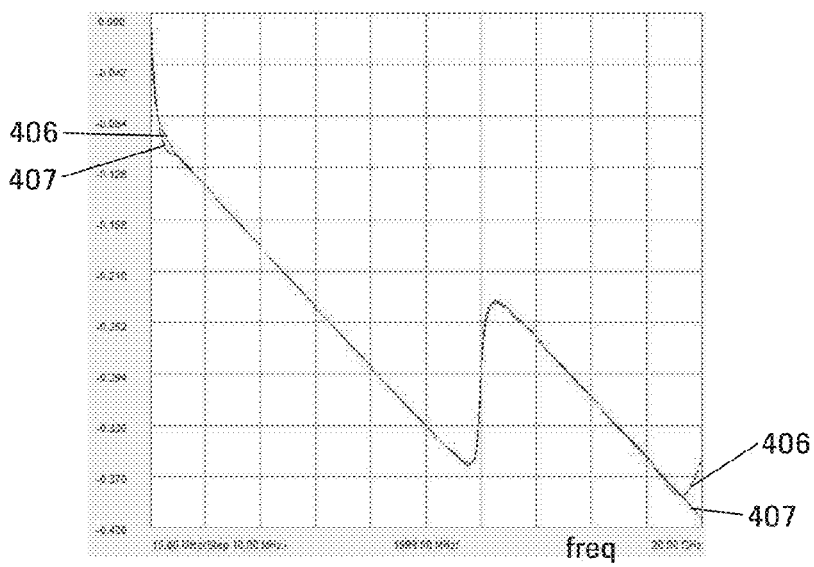

FIG. 7C is a graph showing, at 404, the variation with frequency of the logarithm of the magnitude of the first port return loss S11 of an example of test fixture 10 generated by characterization system 100. The graph also shows, at 405, the variation with frequency of the logarithm of the magnitude of the first port return loss S11 of the example of test fixture 10 measured conventionally. FIG. 7D is a graph showing, at 406, the variation with frequency of the phase of first port return loss S11 of the example of test fixture 10 generated by characterization system 100. The graph also shows, at 407, the variation with frequency of the phase of the first port return loss S11 of the example of test fixture 10 measured conventionally. Correlation between the characteristics is good apart from near the maximum frequency of interest. The discrepancy is due to the time gating to which gating processor 114 subjects first time-gated measurement signal TGMS1. To characterize a test fixture specified for use in a given frequency range of interest that has a maximum frequency, the effects of time gating can be mitigated by measuring over a frequency range having a maximum frequency greater than, e.g., 10% greater than, the maximum frequency of the frequency range of interest.

FIGS. 8A and 8B are block diagrams showing simplified examples of insertion loss generator 124. FIG. 8A is a block diagram showing an example 420 of an insertion loss generator suitable for use in an embodiment of characterization system 100 in which test system 110 generates second time-gated measurement signal TGMS2 as a frequency-domain signal. Second time-gated measurement signal TGMS2 in the frequency domain represents the two-way insertion loss TWIL at the first port 30 of test fixture 10. To obtain the first port reverse insertion loss P1RIL from two-way insertion loss TWIL, the two-way insertion loss is divided by the reflection coefficient Γ of the termination at the second port 40 of test fixture 10 to generate a quotient, and the square root of the quotient is calculated to generate the first port reverse insertion loss P1RIL. In other words:

$$P1RIL = \sqrt{TWIL/\Gamma} \quad (1)$$

Since the components of test fixture 10 are all reciprocal, the result of the square root calculation also provides the first port forward insertion loss P1FIL of test fixture 10 since the first port forward insertion loss is equal to the first port reverse insertion loss.

Insertion loss generator 420 includes a divider 424 and a square root calculator 426 connected in series. Insertion loss generator 420 receives frequency-domain second time-gated measurement signal TGMS2, and receives a reflection coefficient signal RC that represents the reflection coefficient F of the reflective termination 118 at the second port 40 of test fixture 10. Frequency-domain second time-gated measurement signal TGMS2 represents the two-way insertion loss TWIL of test fixture 10. Divider 424 divides second time-gated measurement signal TGMS2 by reflection coefficient RC to generate a quotient Q. Square root calculator 426 calculates the square root of quotient Q. Insertion loss generator 420 outputs the square root of quotient Q as a first port reverse insertion loss signal P1RILS, and as a first port forward insertion loss signal P1FILS. First port reverse insertion loss signal P1RILS and first port forward insertion loss signal P1FILS represent the reverse first insertion loss P1RIL and the forward insertion loss P1FIL, respectively, of the first port 30 of test fixture 10. Insertion loss generator 420 additionally outputs second time-gated measurement signal TGMS2 as two-way insertion loss signal TWILS for use by second port return loss generator 126, as will be described below.

FIG. 8B is a block diagram showing an example 430 of an insertion loss generator suitable for use in an embodiment of characterization system 100 in which test system 110 generates second time-gated measurement signal TGMS2 as a time-domain signal. Elements of insertion loss generator 430 that correspond to elements of insertion loss generator 420 described above with reference to FIG. 8A are indicated using the same reference numerals and will not be described again.

Insertion loss generator 430 includes a time domain to frequency domain transform processor 432, divider 424, and square root calculator 426 connected in series. Insertion loss generator 430 receives time-domain second time-gated measurement signal TGMS2, and receives reflection coefficient signal RC that represents the reflection coefficient F of the reflective termination 118 at the second port 40 of test fixture 10. Time domain to frequency domain transform processor 432 receives time-domain second time-gated measurement signal TGMS2, and transforms measurement signal TGMS2 from the time domain to the frequency domain for output as two-way insertion loss signal TWILS, and for input to divider 424. Structure and operation of insertion loss generator 430 is otherwise the same as that of insertion loss generator 420, and will therefore not be described further.

FIG. 8C is a graph showing, at 434, the variation with frequency of the logarithm of the magnitude of the first port forward insertion loss S21 of an example of test fixture 10 generated by characterization system 100. The graph also shows, at 435, the variation with frequency of the logarithm on the magnitude of the first port forward insertion loss S21 of the example of test fixture 10 measured conventionally. The difference between curve 434 and curve 435 near the maximum frequency of interest can again be reduced by measuring over a frequency range having a maximum frequency greater than the maximum frequency of the frequency range of interest. FIG. 8D is a graph showing the variation with frequency of the phase of first port forward insertion loss S21 of the example of test fixture 10 generated by characterization system 100 and the variation with frequency of the phase of the first port forward insertion loss S21 of the example of test fixture 10 measured conventionally. The curves shown in FIG. 8D are so closely superimposed that they cannot be distinguished from one another.

Figure 9A:
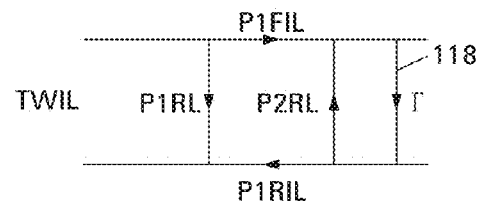
FIG. 9A is a signal flow diagram of an example of a test fixture having a reflective termination at its second port.

FIG. 9A is a signal flow diagram showing an example of test fixture 10 having a reflective termination 118 at second port 40. Reflective termination 118 has a reflection coefficient F. The signal flow diagram shows the relationship between two-way insertion loss TWIL and the scattering parameters P1RL, P1RIL, P1FIL and P2RL of the test fixture. The relationship is described by the following equation:

$$\text{TWIL} = P1RL + P1FIL*\Gamma*P1RIL/1 - P2RL*\Gamma \quad (2).$$

Signals that represent TWIL, P1RL, P1RIL, P1FIL have been generated by first port return loss generator 122 and insertion loss generator 124, as described above. A value for second port return loss P2RL can be determined from TWIL, P1RL, P1RIL, P1FIL by rearranging equation (2) as follows:

$$P2RL = (1 - P1FIL*\Gamma*P1RIL/TWIL - P1RL)*\Gamma \quad (3).$$

Figure 9B:
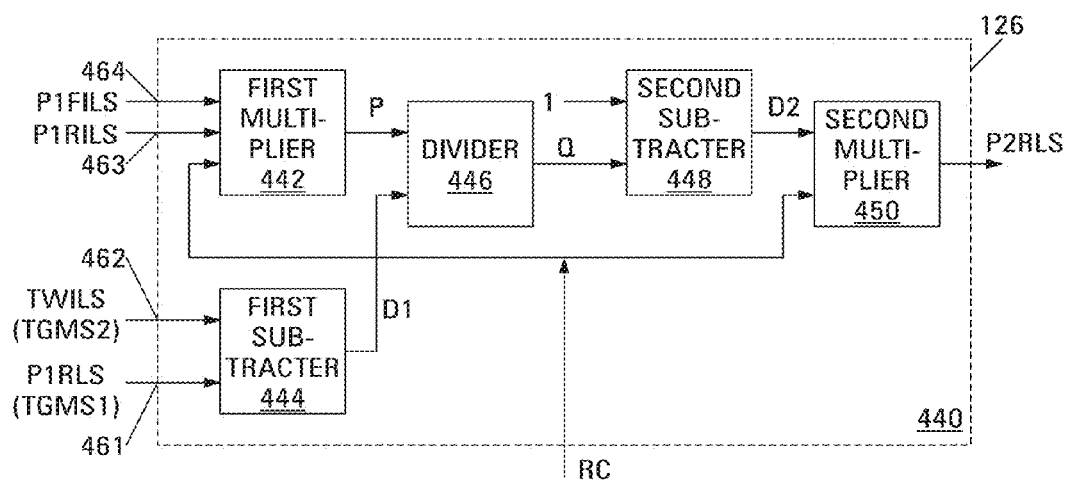
FIG. 9B is a block diagram showing a simplified example of a second port return loss generator.

FIG. 9B is a block diagram showing a simplified example 440 of a second port return loss generator suitable for use in an embodiment of characterization system 100. Second port return loss generator 440 includes inputs 461-464. Second port return loss generator 440 receives first port return loss signal P1RLS from first port return loss generator 122 at input 461, and receives at inputs 462-464 two-way insertion loss signal TWILS, first port reverse insertion loss signal P1RILS, and first port forward insertion loss signal P1FILS, respectively, from insertion loss generator 124. In an embodiment in which test system 110 generates time-gated measurement signals TGMS1 and TGMS2 as frequency-domain signals, first time-gated measurement signal TGMS1 and second time-gated measurement signal TGMS2 received directly from gating processor 114 may optionally be substituted for first port return loss signal P1RLS and the two way insertion loss signal TWIL. Second port return loss generator 440 additionally receives a reflection coefficient signal RC that represents the reflection coefficient F of reflective termination 118. In another embodiment (not shown), one or more quantities that represent the reflection coefficient of, for example, an open circuit termination and/or a short-circuit termination is built in to second port return loss generator 440.

Second port return loss generator 440 includes a first multiplier 442, a first subtracter 444, a divider 446, a second subtracter 448, and a second multiplier 450. First multiplier 442 multiplies first port reverse insertion loss signal P1RIL, first port forward insertion loss signal P1FIL, and reflection coefficient signal RC to generate a product P. First subtracter 444 subtracts first port return loss signal P1RLS from two-way insertion loss signal TWILS to generate a first difference D1. In an embodiment in which first time-gated measurement signal TGMS1 and second time-gated measurement signal TGMS2 are frequency-domain signals, first subtracter 444 optionally subtracts first time-gated measurement signal TGMS1 from second time-gated measurement signal TGMS2 instead. Divider 446 divides product P by difference D1 to generate a quotient Q. Second subtracter 448 subtracts quotient Q from unity to generate a second difference D2. Second multiplier 450 multiplies second difference D2 by reflection coefficient signal RC to generate second port return loss signal P2RLS that represents the second port return loss P2RL of test fixture 10.

Since in embodiments of characterization system 100 in which time-gated measurement signals TGMS1 and TGMS2 are time-domain signals, second port return loss generator 126 receives first port return loss signal P1RLS from first port return loss generator 122, and receives two-way insertion loss signal TWILS, first port reverse insertion loss signal P1RILS, and first port forward insertion loss signal P1FILS from insertion loss generator 124, an embodiment of second port return loss generator 126 that generates second port return loss signal P2RLS from first time-gated measurement signal TGMS1 and second time-gated measurement signal TGMS2 can be regarded as including the circuitry of first port return loss generator 122 and insertion loss generator 124 in addition to the circuitry shown in FIG. 9B. Moreover, since in embodiments of characterization system 100 in which time-gated measurement signals TGMS1 and TGMS2 are frequency-domain signals, second port return loss generator 126 receives first port reverse insertion loss signal P1RILS and first port forward insertion loss signal P1FILS from insertion loss generator 124, an embodiment of second port return loss generator 126 that generates second port return loss signal P2RLS from first time-gated measurement signal TGMS1 and second time-gated measurement signal TGMS2 can be regarded as including the circuitry of insertion loss generator 124 in addition to the circuitry shown in FIG. 9B.

Figure 9C:
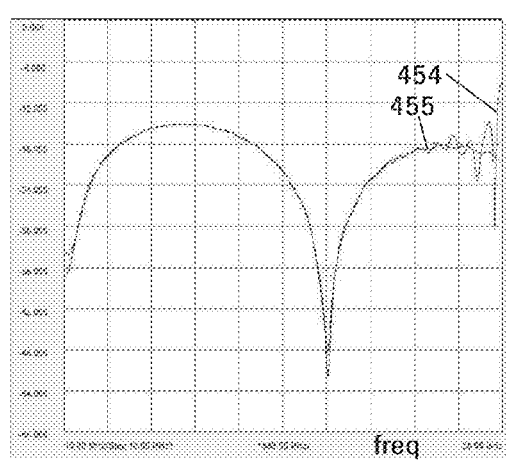
FIGS. 9C and 9D are graphs showing the variation with frequency of the logarithm of the magnitude and the phase, respectively, of the second port return loss S22 of an example of a test fixture.
Figure 9D:
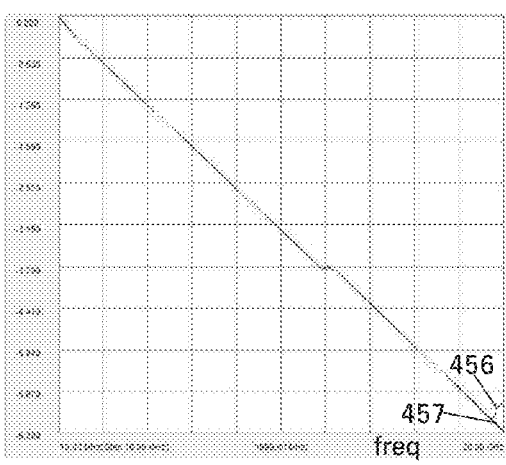

FIG. 9C is a graph showing, at 454, the variation with frequency of the magnitude of the second port return loss S22 of an example of test fixture 10 generated by characterization system 100. The graph also shows, at 455, the variation with frequency of the magnitude of the second port return loss S22 of the example of test fixture 10 measured conventionally. FIG. 9D is a graph showing, at 456, the variation with frequency of the phase of second port return loss S22 of the example of test fixture 10 generated by characterization system 100. The graph also shows, at 457, the variation with frequency of the phase of the second port return loss S22 of the example of test fixture 10 measured conventionally. Curve 454 exhibits significant ripples towards the high frequency end of the spectrum. Part of the ripple is due to gating effects in the first port return loss S11 of test fixture 10, and again may be mitigated by measuring over a frequency range having a maximum frequency greater than the maximum frequency of the frequency range of interest.

Another contribution to the ripple shown in FIG. 9C is a small delay error in first port forward insertion loss P1FIL and first port reverse insertion loss P1RIL. The transform of equation (3) can be analyzed in two parts: the transform of unity is a delta function at time zero (the temporal position of first port 30), and the transform of (P1FIL*P1RIL)/(TWIL-P1RL) is a delta function plus second port return loss P2RL.

FIG. 10A is a graph showing the impulse response of an example of the second part of equation (3). FIG. 10B is a graph showing part of the impulse response shown in FIG. 10A on an expanded time scale. If there is no error in the delay of the product P1FIL*P1RIL of the first port forward insertion loss and the first port reverse insertion loss, the delta function at time zero from the two parts of equation (3) will exactly cancel, and the difference between the two parts of equation (3) will provide second port return loss P2RL. But if there is even a slight error in the delay of P1FIL*P1RIL, the two delta functions will not cancel, but instead will leave a residual error around time zero. The example shown in FIGS. 10A and 10B has a peak 1.005 ps after time zero instead of at time zero.

FIG. 10C is a graph showing an example of the impulse response of the second port return loss P2RL as determined by second port return loss generator 440. The return loss shown exhibits ripples resulting from the delay error exemplified in FIGS. 10A and 10B. The small delay error shown in FIGS. 10A and 10B causes ripples in the impulse response of the second port return loss P2RL before time zero, as shown at 458 in FIG. 10C. A larger delay error than that exemplified may also cause a peak and a dip in second port return loss P2RL as determined by second port return loss generator 126.

In characterization system 100, the above-described delay error is compensated for by modifying second port return loss generator 126 to apply time gating to second port return loss signal P2RLS. Second port return loss signal P2RLS output by second multiplier 450 (FIG. 9B) can be regarded as a preliminary second port return loss signal P2RLSP. FIG. 10D is a graph showing the impulse response of an example of preliminary second port return loss signal P2RLSP. The preliminary second port return loss signal is subject to time gating using a third gating function to generate a time-gated second port return loss signal. The third gating function is temporally disposed about the second port.

FIG. 10D also shows an example of a third gating window 460 used to define the third gating function. Third gating window 460 has a start time TT3 and a stop time PT3. In the example shown, start time TT3 is at a time delayed relative to time zero (corresponding to the temporal position of the first port 30 of test fixture 10) by a multiplier M times the rise time RT of amplitude step 152 (FIG. 2A). This locates start time TT3 an elapsed time ET3 before step time ST, the temporal position of amplitude step 152. In the example shown, stop time PT3 is at a time delayed by elapsed time ET3 relative to step time ST. The examples of start time TT3 and stop time PT3 just described center third gating window 460 on the temporal position of reflective termination 118. In an example, multiplier M is 10. In other examples, multiplier M is an integer or non-integer greater than or less than 10.

A third gating window start and stop time calculator and a third gating function calculator (not shown) added to gating function generator 350 described above with reference to FIG. 6A can be used to determine the start time TT3 and the stop time PT3 of the third gating window, and to generate a third gating function signal GF3 that represents the third gating function from start time TT3, stop time PT3, and a gating characteristic that defines the gating characteristic of the third gating function. Alternatively, one of the gating window start and stop time calculators 358, 360 and one of the gating function calculators 362, 364 of gating function generator 350 can be re-used to generate the third gating function signal.

Figure 11A:
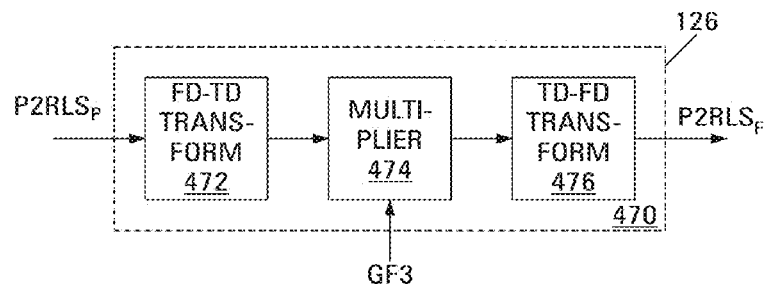
FIGS. 11A and 11B are block diagrams showing simplified examples of a delay mitigation module that may be added to a second port return loss generator to mitigate the effects of a delay error.

FIG. 11A is a block diagram showing a simplified example 470 of a delay mitigation module that may be added to second port return loss generator 126 to mitigate the effects of a delay error. Delay mitigation module 470 includes a frequency domain to time domain transform processor 472, a multiplier 474 and a time domain to frequency domain transform processor 476. Frequency domain to time domain transform processor 472 receives preliminary second port return loss signal $P2RLS_P$ from second multiplier 450 (FIG. 9B). Preliminary second port return loss signal $P2RLS_P$ represents the return loss of the second port 40 of test fixture generated by second port return loss generator 440. Frequency domain to time domain transform processor 472 transforms the preliminary second port return loss signal from the frequency domain to the time domain to generate a time-domain preliminary second port return loss signal. Multiplier 474 receives the time-domain preliminary second port return loss signal and third gating function signal GF3. Multiplier 474 subjects the time-domain preliminary second port return loss signal to time gating using the third gating function by multiplying the time-domain preliminary second port return loss signal by third gating function signal GF3 in a manner similar to that described above with reference to FIG. 5A to generate a time-gated second port return loss signal. Time domain to frequency domain transform processor 476 transforms time-gated second port return loss signal from the time domain to the frequency domain to generate a final second port return loss signal $P2RLS_F$. Final second port return loss signal $P2RLS_F$ is a frequency-domain signal that represents the second port return loss of test fixture 10 in which ripple effects due to delay mismatch are substantially mitigated.

Figure 11B:
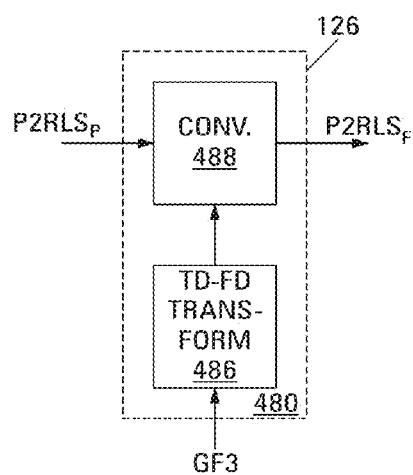

FIG. 11B is a block diagram showing another simplified example 480 of a delay mitigation circuit that may be included in second port return loss generator 126 to mitigate the effects of a delay error. Delay mitigation circuit 480 includes a convolution processor 488 and a time domain to frequency domain transform processor 486. Time domain to frequency domain transform processor receives third gating function signal GF3 generated as described above, and transforms the third gating function signal from the time domain to frequency domain to generate a frequency-domain third gating function signal $GF3_F$. Convolution processor 488 receives preliminary second port return loss signal from second multiplier 450 (FIG. 9B) and frequency-domain third gating function signal $GF3_F$. Convolution processor 488 subjects the preliminary second port return loss signal to time gating using the third gating function by subjecting the preliminary second port return loss signal and the frequency-domain third gating function signal to convolution processing in a manner similar to that described above with reference to FIG. 5B to generate above-described final second port return loss signal $P2RLS_F$.

Figure 11C:
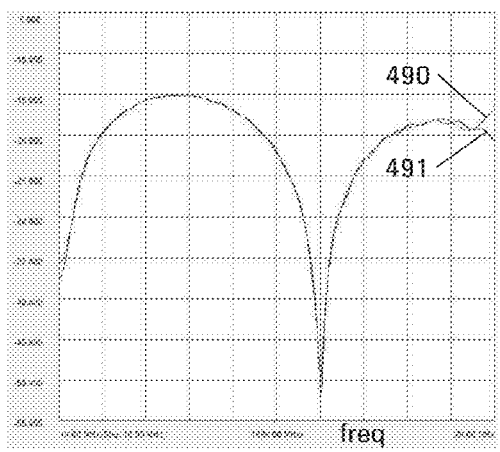
FIGS. 11C and 11D are graphs showing the variation with frequency of the logarithm of the magnitude and the phase, respectively, of the second port return loss S22 of an example of a test fixture generated by an example of a second return loss generator with a delay mitigation module.
Figure 11D:
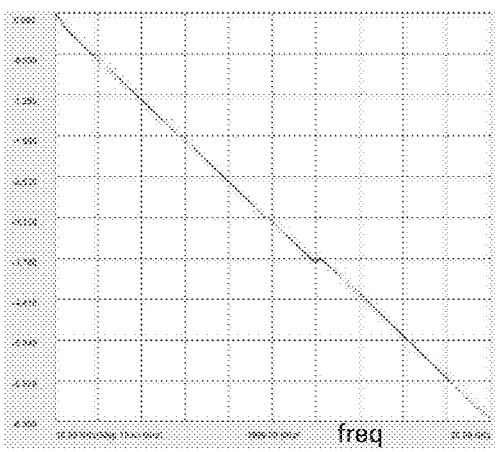

FIG. 11C is a graph showing, at 490, the variation with frequency of the logarithm of the magnitude of the second return loss S22 of an example of test fixture 10 generated by characterization system 100. The graph also shows, at 491, the variation with frequency of the logarithm of the magnitude of the second port return loss S22 of the example of test fixture 10 measured conventionally. FIG. 11D is a graph showing the variation with frequency of the phase of second port return loss S22 of the example of test fixture 10 generated by characterization system 100 and the variation with frequency of the phase of the second port return loss S22 of the example of test fixture 10 measured conventionally. The curves shown in FIG. 11 are so closely superimposed that they cannot be distinguished from one another.

The example of test fixture 10 shown in FIG. 1 is for testing single-ended DUTs having a single-ended input connection. In test fixture 10, first port 30 and second port 40 are single-ended ports interconnected by a single strip line 50. First port 30 is connected by test cable 117 to a single-ended test port 116 of test instrument 112. Second port 40 is connected to a single-ended input of the DUT. Other test fixtures (not shown) are differential test fixtures for testing DUTs having differential input connections. In a differential test fixture, first port 30 and second port 40 are differential ports interconnected by a pair of strip lines 50. First port 30 is connected by test cable 117 to a differential test port 116 of test instrument 112. Second port 40 is connected to a differential input of the DUT. To characterize a differential test fixture using above-described characterization system 100, a test instrument capable of generating a differential one-port reflection test signal and of outputting such test signal to the differential first port of the test fixture is used as test instrument 112. The test instrument should also be capable of receiving a differential one-port reflection measurement signal from the differential first port of the test fixture, and of extracting the differential one-port reflection measurement from the one-port reflection test signal. Test instrument 112 is used to generate a differential one-port reflection measurement signal and a common-mode one-port reflection measurement signal in response to a differential one-port reflection test signal and a common-mode one-port reflection test signal, respectively.

Gating processor 114 operates a first time in the manner described above to subject the differential one-port reflection measurement signal to time gating using two different gating functions to generate respective time-gated differential measurement signals. Scattering parameter generator 120 operates a first time in the manner described above to generate signals that represent differential scattering parameters, namely, first port differential return loss Sdd11, first port differential reverse insertion loss Sdd12, first port differential forward insertion loss Sdd21 and second port differential return loss Sdd22 from the time-gated differential measurement signals.

Gating processor 114 operates a second time in the manner described above to subject the common-mode one-port reflection measurement signal to time gating using the two different gating functions to generate respective time-gated common-mode measurement signals. Scattering parameter generator 120 operates a second time in the manner described above to generate signals that represent common-mode scattering parameters, namely, first port common-mode return loss Scc11, first port common-mode reverse insertion loss Scc12, first port common-mode forward insertion loss Scc21 and second port common-mode return loss Scc22 from the time-gated common-mode measurement signals.

Scattering parameter generator 120 outputs above-described scattering parameter signals P1RLS, P1RILS, P1FILS and P2RLS that represent the scattering parameters of test fixture 10 to test instrument 112. Any physical reflective termination connected to the second port 40 of test fixture 10 is removed. A port of a device under test (DUT—not shown) is then connected to second port 40. Test instrument 112 is then used to measure scattering parameters of the combination of the DUT and test fixture 10. The test instrument then uses the scattering parameter signals received from scattering parameter generator 120 to de-embed the scattering parameters of the test fixture from the scattering parameters of the combination, which allows the scattering parameters of the DUT alone to be determined. Alternatively, scattering parameter generator 120 outputs scattering parameter signals P1RLS, P1RILS, P1FILS and P2RLS to an external processor (not shown). The external processor additionally receives from test instrument 112 signals that represent the scattering parameters of the combination of test fixture 10 and the DUT, and de-embeds the scattering parameters of the DUT from those of the combination to calculate the scattering parameters of the DUT.

In a typical implementation of test fixture characterization system 100, test instrument 112 is typically a commercially-available general-purpose test instrument. Embodiments of gating processor 114 and scattering parameter generator 120, and the modules thereof described in this disclosure, may be constructed from discrete components, small-scale or large-scale integrated circuits, suitably-configured application-specific integrated circuits (ASICs) or field-programmable gate arrays (FPGAs) and/or other suitable hardware. Gating processor 114 and scattering parameter generator 120, and the modules thereof may alternatively or additionally be constructed using a one or more digital signal processors (DSPs), microprocessors, microcomputers or computers with internal or external memory operating in response to a program fixed in a computer-readable medium. A device, such as a DSP, a microprocessor, microcomputer or computer, capable of executing a program will be referred to herein as a computer.

In computer-based embodiments, the various modules described herein may be ephemeral, and may only exist temporarily as the program executes. In such embodiments, the program could be conveyed to the computer on which it is to run by embodying the program in a suitable computer-readable medium, such as a set of floppy disks, a CD-ROM, a DVD-ROM, a BD-ROM, a flash drive, or a read-only memory. Alternatively, the program could be transmitted to the computer on which it is to run from a computer-readable medium in another computer by a suitable physical or wireless data link, and be stored in a memory device in the computer on which it is to run.

Where multiple modules, e.g., subtractors, of the same or a similar type are described, the multiple modules may be replaced by a single module that is used serially. Moreover, single modules that are described as processing or generating multiple signals serially may be replaced by multiple modules, each of which processes or generates a respective single signal.

Figure 12:
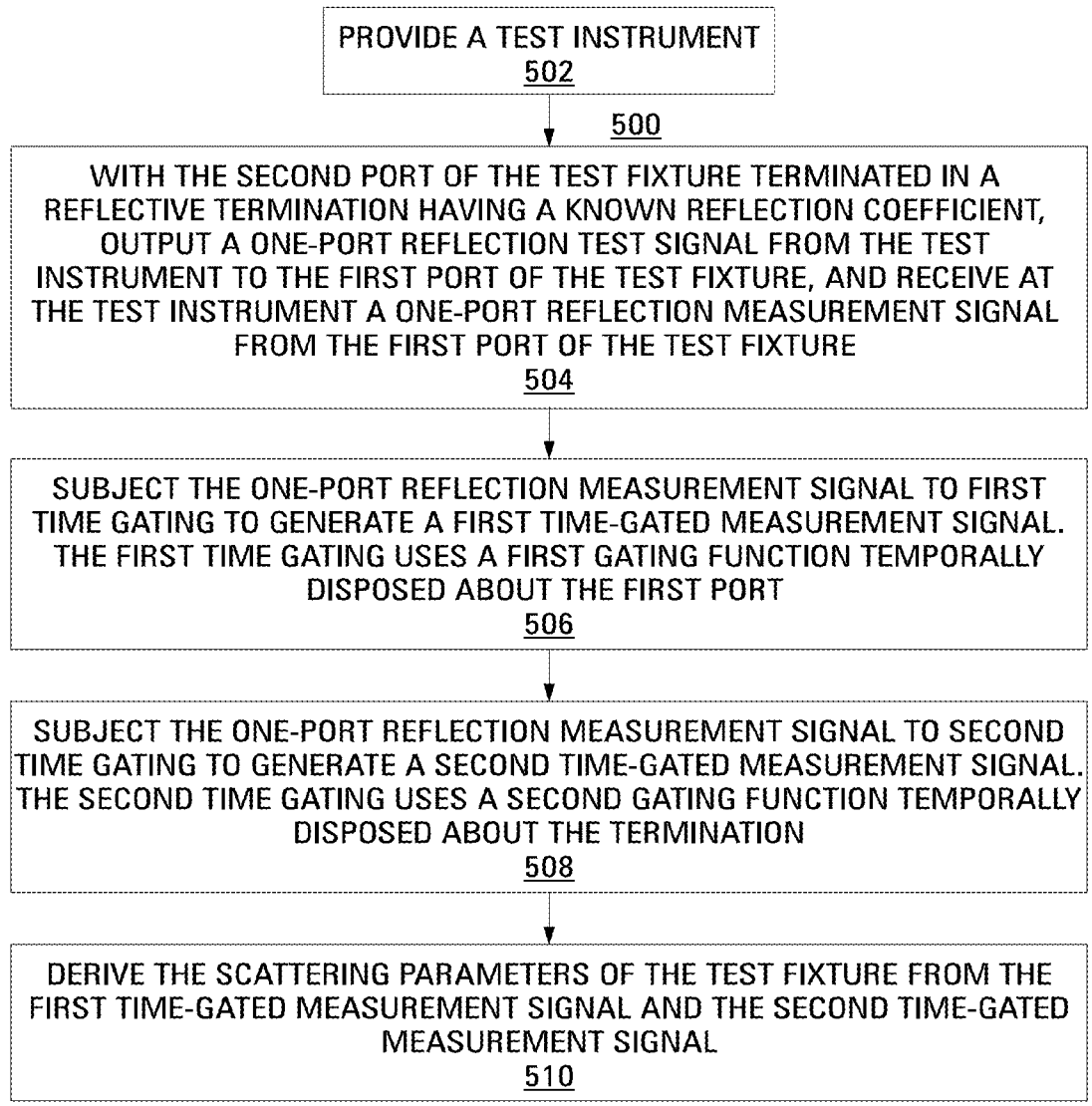
FIG. 12 is a flowchart showing an example of a method in accordance with the disclosure of measuring scattering parameters of a test fixture having a first port and a second port.

FIG. 12 is a flowchart showing an example 500 of a method in accordance with the disclosure of measuring scattering parameters of a test fixture having a first port and a second port. In the method, in block 502, a test instrument is provided. In block 504, with the second port of the test fixture terminated in a reflective termination having a known reflection coefficient, a one-port reflection test signal is output from the test instrument to the first port of the test fixture, and a one-port reflection measurement signal is received from the first port of the test fixture at the test instrument. In block 506, the one-port reflection measurement signal is subject to first time gating to generate a first time-gated measurement signal. The first time gating uses a first gating function temporally disposed about the first port. In block 508, the one-port reflection measurement signal is subject to second time gating to generate a second time-gated measurement signal. The second time gating uses a second gating function temporally disposed about the termination. In block 510, the scattering parameters of the test fixture are derived from the first time-gated measurement signal and the second time-gated measurement signal.

In an example in which the first time-gated measurement signal is a time-domain signal, a return loss at the first port of the test fixture, a first one of the scattering parameters, is derived in block 510 by transforming the first time-gated measurement signal from the time domain to the frequency domain to provide a first port return loss signal representing the return loss at the first port of the test fixture.

In an example in which the first time-gated measurement signal is a frequency-domain signal, the return loss at the first port of the test fixture is derived in block 510 by outputting the first time-gated measurement signal to provide the first port return loss signal.

Figure 13A:
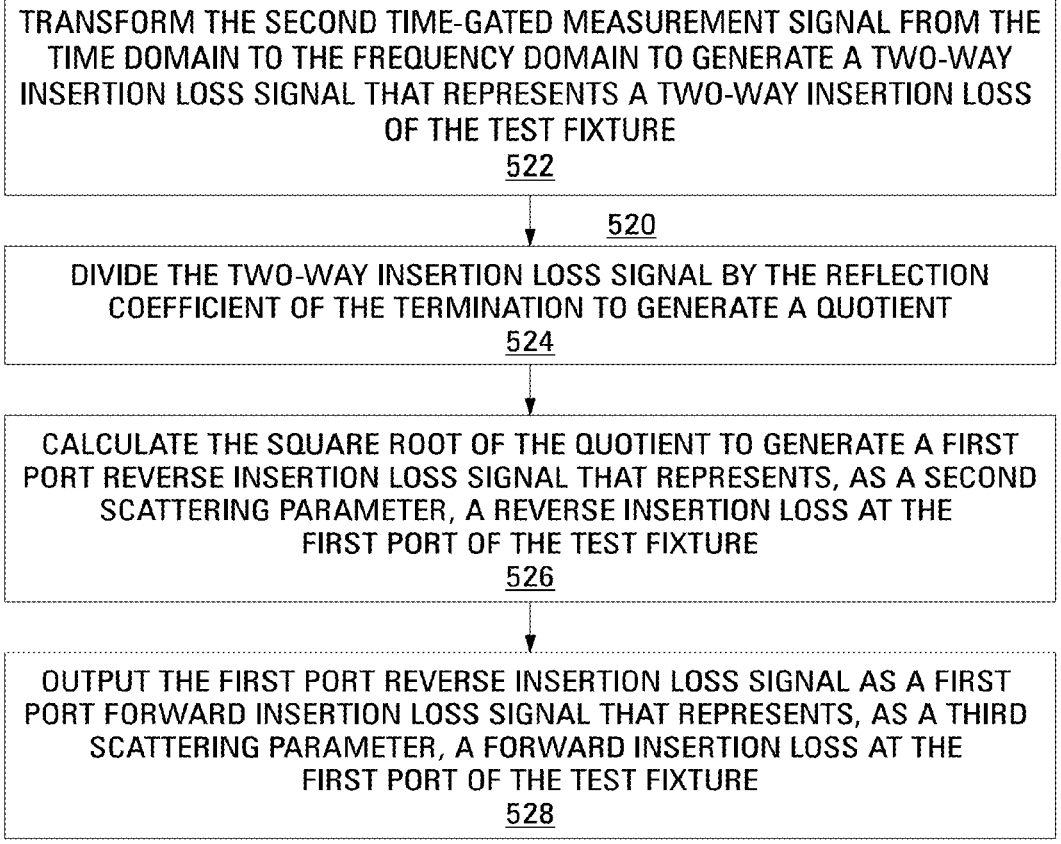
FIGS. 13A and 13B are flow charts showing examples of methods of deriving a first port reverse insertion loss signal and a first port forward insertion loss signal from a second time-gated measurement signal.

FIG. 13A is a flowchart showing an example 520 of a method of deriving, in block 510, a first port reverse insertion loss signal that represents, as a second scattering parameter, a reverse insertion loss at the first port of the test fixture, and a first port forward insertion loss signal that represents, as a third scattering parameter, a forward insertion loss at the first port of the test fixture from a second time-gated measurement signal that is a time-domain signal. In block 522, the second time-gated measurement signal is transformed from the time domain to the frequency domain to generate a two-way insertion loss signal that represents a two-way insertion loss of the test fixture. In block 524, the two-way insertion loss signal is divided by the reflection coefficient of the termination at the second port of the test fixture to generate a quotient. In block 526, the square root of the quotient is calculated to generate the first port reverse insertion loss signal. In block 528, the first port reverse insertion loss signal is additionally output as a first port forward insertion loss signal that represents, as a third scattering parameter, a forward insertion loss at the first port of the test fixture.

Figure 13B:
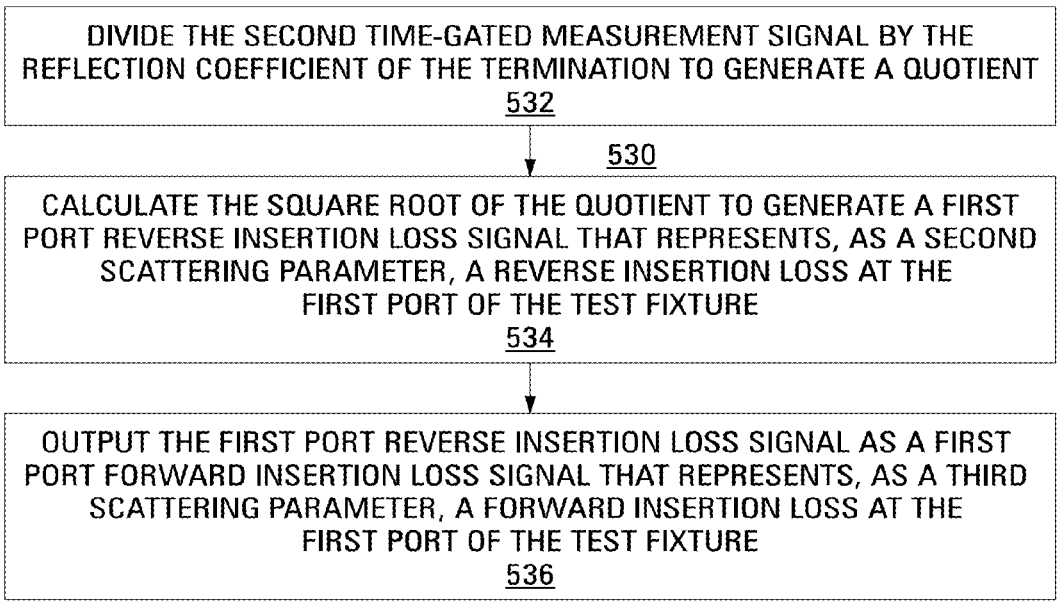

FIG. 13B is a flowchart showing an example 530 of a method of deriving, in block 510, the first port reverse insertion loss signal and the first port forward insertion loss signal from a second time-gated measurement signal that is a frequency-domain signal. In block 532, the second time-gated measurement signal is divided by the reflection coefficient of the termination at the second port of the test fixture to generate a quotient. In block 534, the square root of the quotient is calculated to generate the first port reverse insertion loss signal. In block 536, the first port reverse insertion loss signal is additionally output as the first port forward insertion loss signal.

Figure 14A:
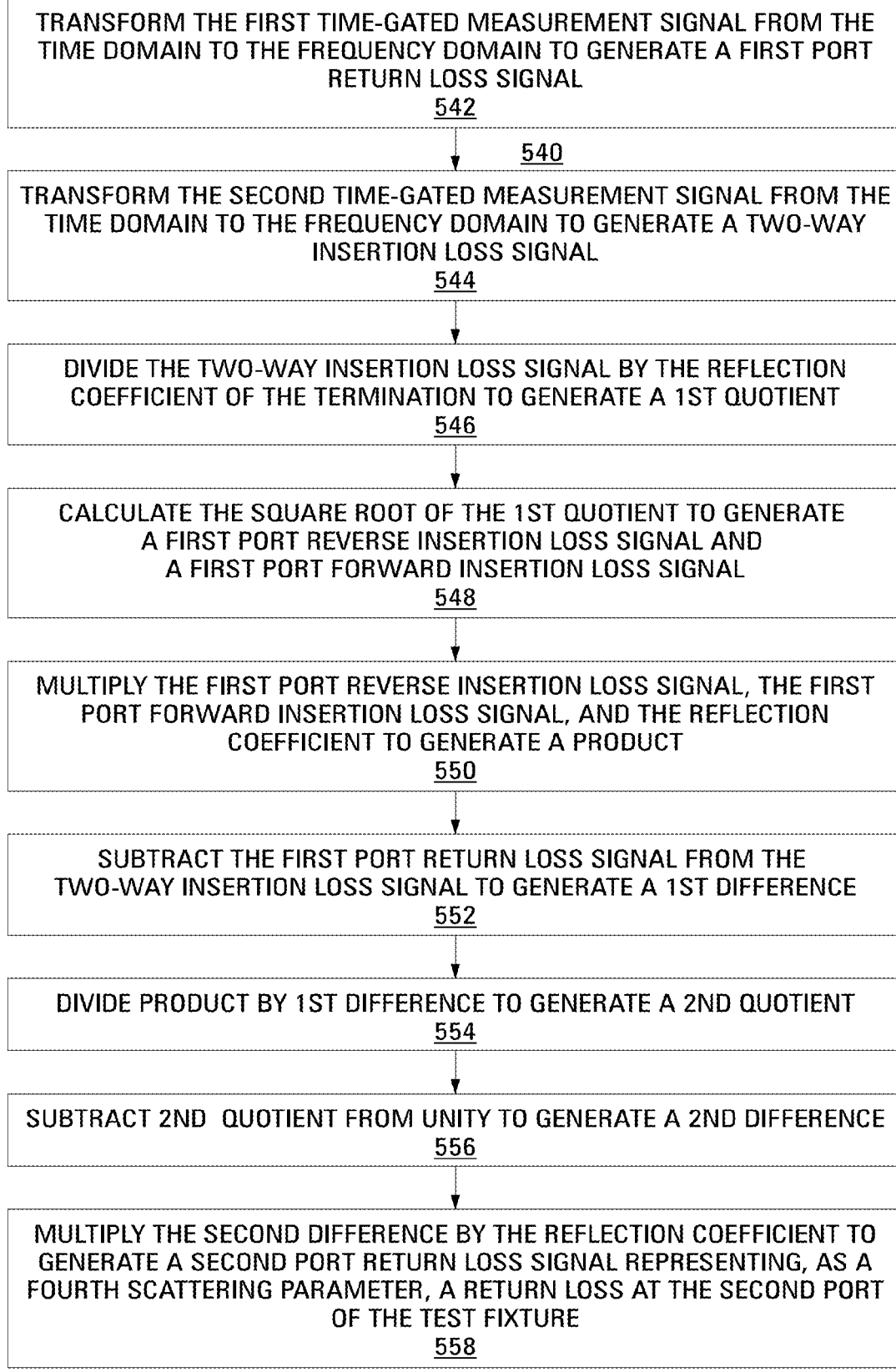
FIG. 14A is a flowchart showing an example of a method of deriving a second port return loss signal from the first time-gated measurement signal and the second time-gated measurement signal.

FIG. 14A is a flowchart showing an example 540 of a method of deriving, in block 510, a second port return loss signal that represents, as a fourth scattering parameter, a return loss at the second port of the test fixture in an example in which the first time-gated measurement signal and the second time-gated measurement signal are time-domain signals. In block 542, the first time-gated measurement signal is transformed from the time domain to the frequency domain to generate a first port return loss signal. In block 544, the second time-gated measurement signal is transformed from the time domain to the frequency domain to generate a two-way insertion loss signal. In block 546, the two-way insertion loss signal is divided by the reflection coefficient of the termination at the second port of the test fixture to generate a first quotient. In block 548, the square root of the first quotient is calculated to generate a first port reverse insertion loss signal and a first port forward insertion loss signal.

In block 550, the first port reverse insertion loss signal, the first port forward insertion loss signal, and the reflection coefficient are multiplied to generate a product. In block 552, the first port return loss signal is subtracted from the two-way insertion loss signal to generate a first difference. In block 554, the product is divided by the first difference to generate a second quotient. In block 556, the second quotient is subtracted from unity to generate a second difference. In block 558, the second difference and the reflection coefficient are multiplied to generate the second port return loss signal that represents the return loss at the second port of the test fixture.

In an example in which the first time-gated measurement signal and the second time-gated measurement signal are frequency-domain signals, a second port return loss signal is derived, in block 510, by a method (not shown) similar to method 540. The method differs from method 540 in that, in block 542, the frequency-domain first time-gated measurement signal is used without transformation as the first port return loss signal, and, in block 544, the frequency-domain second time-gated measurement signal is used without transformation as the two-way insertion loss signal.

Figure 14B:
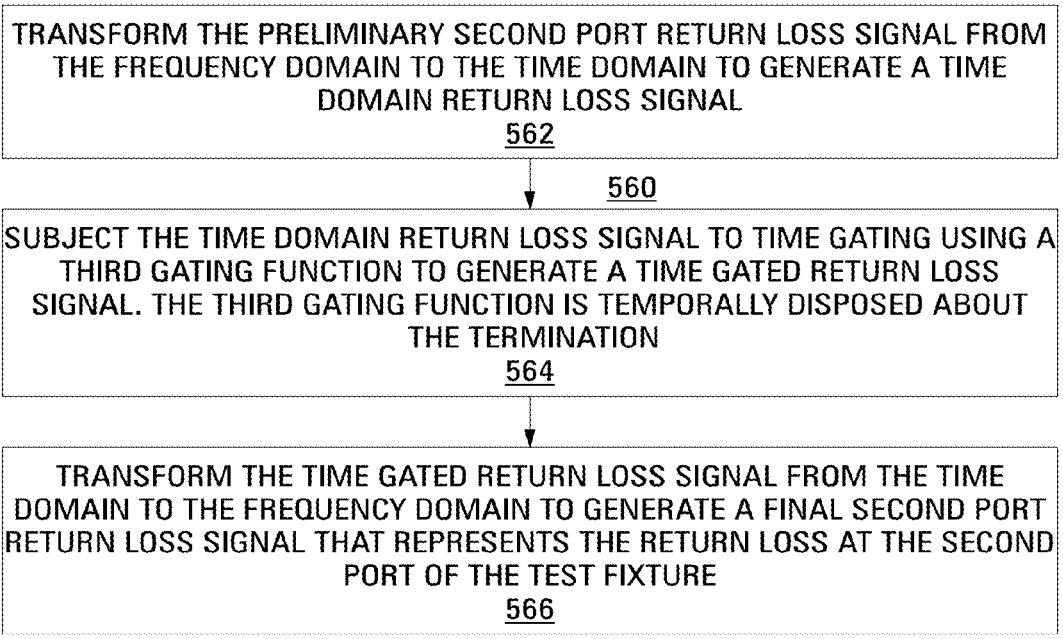
FIGS. 14B and 14C are flow charts showing examples of methods of applying time delay error mitigation to the second port return loss signal.

FIG. 14B is a flow chart showing a first example 560 of additional operations that can be included in method 540 when the second port return loss signal generated in block 558 is subject to excessive ripple. The second port return loss signal generated in block 558 is a preliminary second port return loss signal. In block 562, the preliminary second port return loss signal is transformed from the frequency domain to the time domain to generate a time-domain return loss signal. In block 564, the time-domain return loss signal is subject to time gating with a third gating function to generate a time-gated return loss signal. The third gating function is temporally disposed about the termination at the second port of the test fixture. In block 566, the time-gated return loss signal is transformed from the time domain to the frequency domain to generate a final second port return loss signal that represents the return loss at the second port of the test fixture.

Figure 14C:
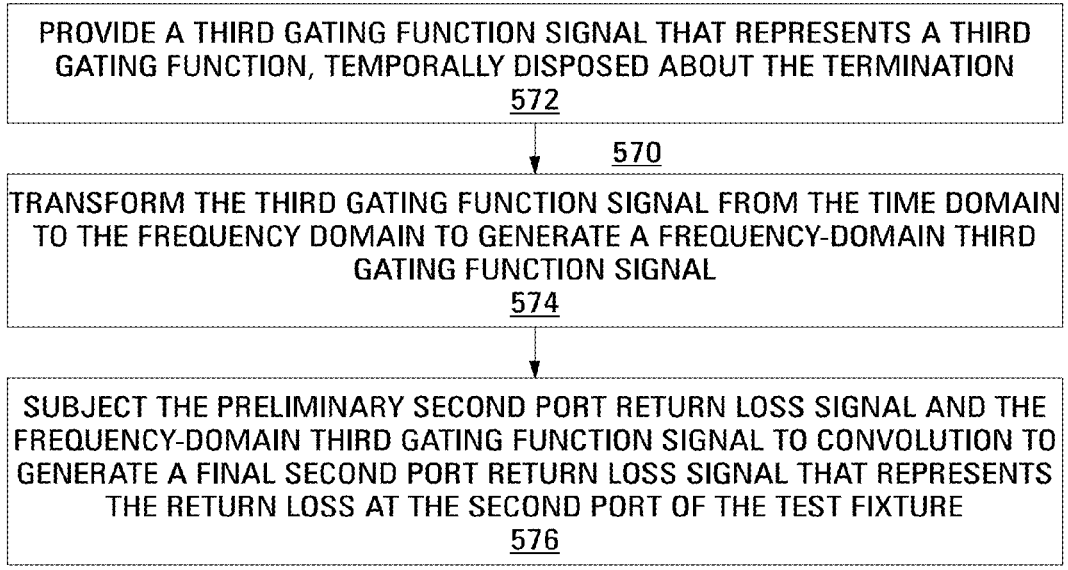

FIG. 14C is a flow chart showing a second example 570 of additional operations that can be included in method 540 when the second port return loss signal generated in block 558 is subject to excessive ripple. The second port return loss signal generated in block 558 is a preliminary second port return loss signal. In block 572, a third gating function signal is provided that represents a third gating function, temporally disposed about the termination at the second port of the test fixture. In block 574, the third gating function signal is transformed from the time domain to the frequency domain to generate a frequency-domain third gating function signal. In block 576, the preliminary second port return loss signal and the frequency-domain third gating function signal are subject to convolution to generate the final second port return loss signal.

In some embodiments of method 500 described above with reference to FIG. 12, in which the test fixture is specified for use over a frequency range of interest having a maximum frequency, the deriving performed in block 510 is performed over a frequency range having a maximum frequency greater than the maximum frequency of the frequency range of interest.

FIGS. 15A-15D are flow charts showing examples of the processing performed in blocks 506 and 508 of method 500 described above with reference to FIG. 12 to subject the one-port reflection measurement signal to first time gating and second time gating, respectively. In all of the examples shown, the first gating function and the second gating function are represented by respective time-domain signals.

FIG. 15A shows an example 600 in which one-port reflection measurement signal OPRMS, first time-gated measurement signal TGMS1, and second time-gated measurement signal TGMS2 are all time-domain signals. In block 602, the one-port reflection measurement signal and the first gating function signal are multiplied to generate the first time-gated measurement signal as a time-domain signal. In block 604, the one-port reflection measurement signal and the second time-domain gating function signal are multiplied to generate the second time-gated measurement signal as a time-domain signal.

FIG. 15B shows an example 610 in which one-port reflection measurement signal OPRMS, first time-gated measurement signal TGMS1, and second time-gated measurement signal TGMS2 are all frequency-domain signals. In block 612, the first gating function signal and the second gating function signal are transformed from the time domain to the frequency domain to generate a first frequency-domain gating function signal and a second frequency-domain gating function signal, respectively. In block 614, the first frequency-domain gating function signal and the one-port reflection measurement signal are subject to convolution to generate the first time-gated measurement signal as a frequency-domain signal. In block 616, the second frequency-domain gating function signal and the one-port reflection measurement signal are subject to convolution to generate the second time-gated measurement signal as a frequency-domain signal.

Figure 15C:
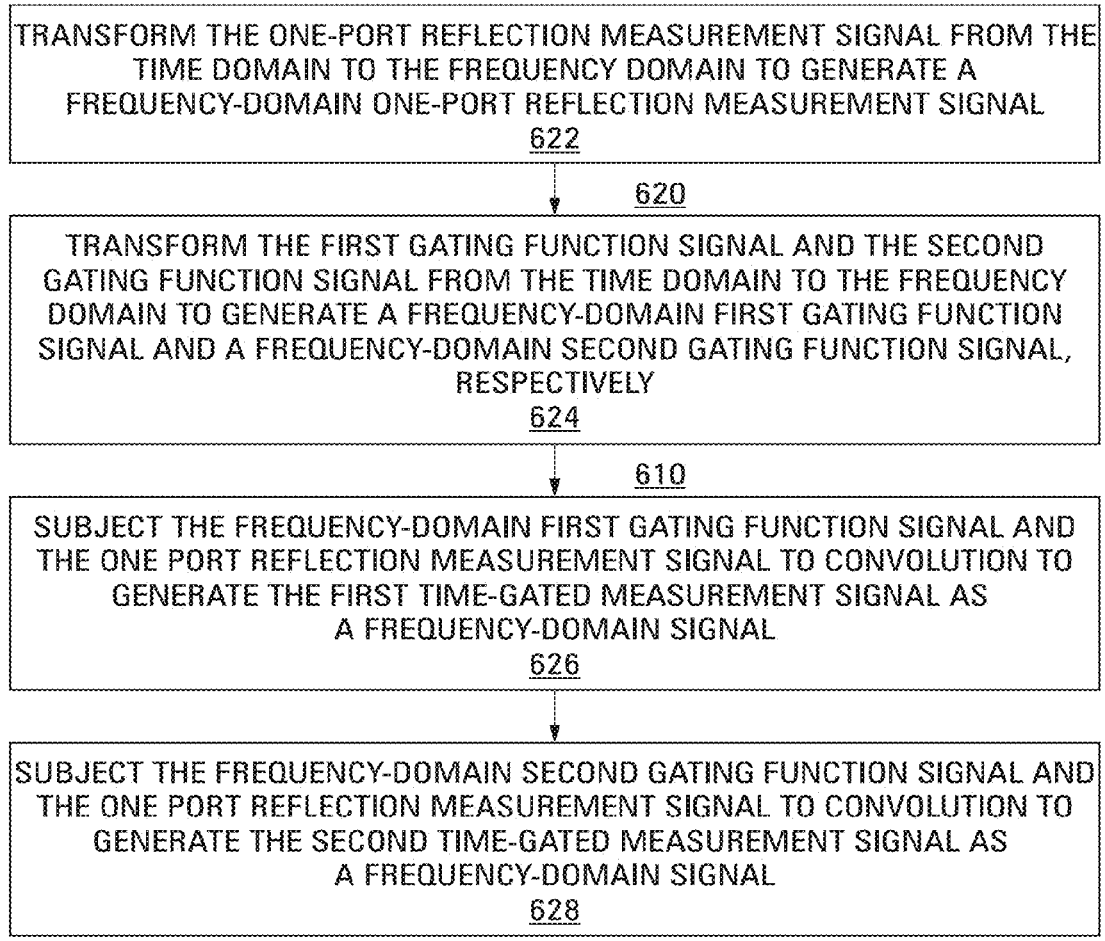

FIG. 15C shows an example 620 in which one-port reflection measurement signal OPRMS is a time-domain signal, and first time-gated measurement signal TGMS1 and second time-gated measurement signal TGMS2 are frequency-domain signals. In block 622, the one-port reflection measurement signal is transformed from the time domain to the frequency domain to generate a frequency-domain one-port reflection measurement signal. In block 624, the first gating function signal and the second gating function signal are transformed from the time domain to the frequency domain to generate a frequency-domain first gating function signal and a frequency-domain second gating function signal, respectively. In block 626, the frequency-domain first gating function signal and the frequency-domain one-port reflection measurement signal are subject to convolution to generate the first time-gated measurement signal as a frequency-domain signal. In block 628, the frequency-domain second gating function signal and the frequency-domain one-port reflection measurement signal are subject to convolution to generate the second time-gated measurement signal as a frequency-domain signal.

Figure 15D:
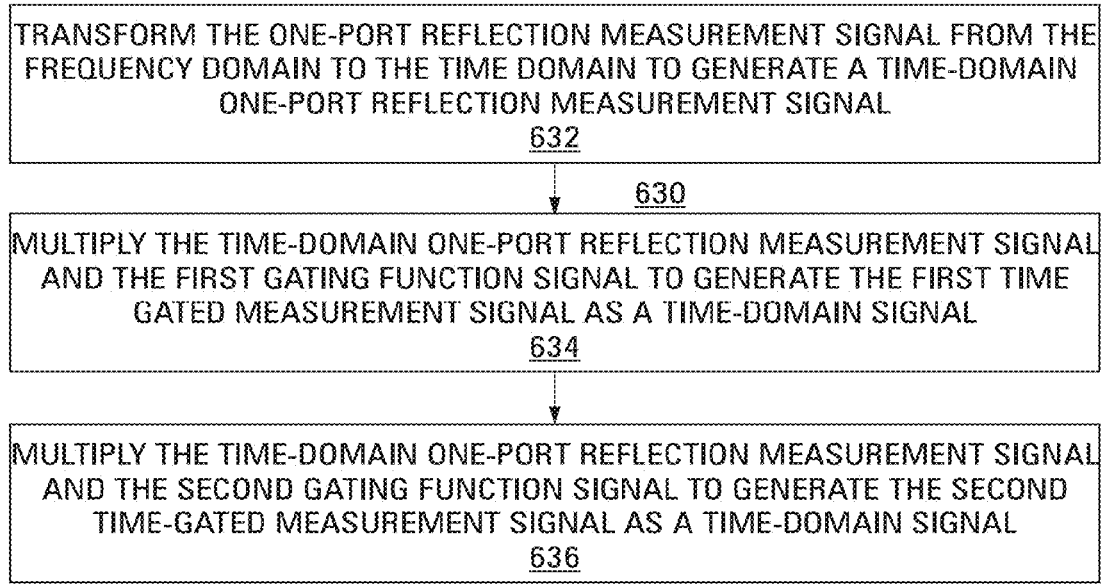

FIG. 15D shows an example 630 in which one-port reflection measurement signal OPRMS is a frequency-domain signal, and first time-gated measurement signal TGMS1 and second time-gated measurement signal TGMS2 are time-domain signals. In block 632, the one-port reflection measurement signal is transformed from the frequency domain to the time domain to generate a time-domain one-port reflection measurement signal. In block 634, the time-domain one-port reflection measurement signal and the first gating function signal are multiplied to generate the first time-gated measurement signal as a time-domain signal. In block 636, the time-domain one-port reflection measurement signal and the second gating function signal are multiplied to generate the second time-gated measurement signal as a time-domain signal.

In an example of method 500, the reflective termination is one of an open circuit and a short circuit.

In an example of method 500 in which the first port and the second port of the test fixture are single-ended ports, the deriving performed in block 510 derives single-ended scattering parameters S11, S12, S21, and S22 for the test fixture from the first time-gated measurement signal and the second time-gated measurement signal.

Figure 16:
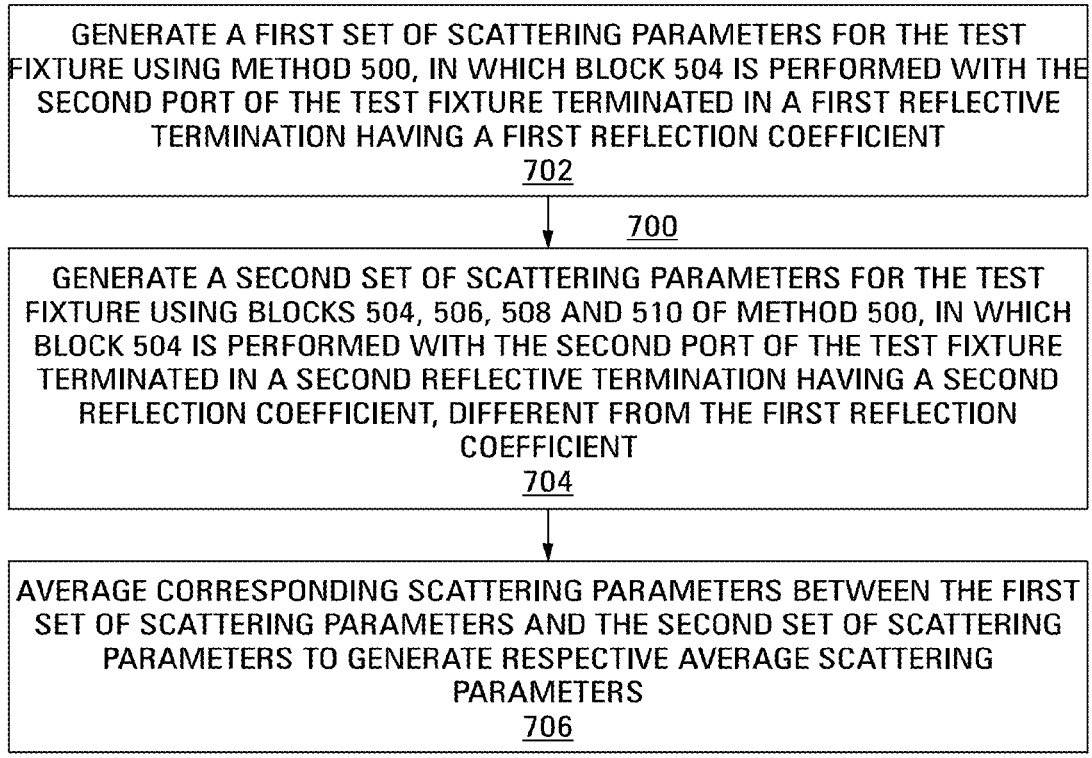
FIG. 16 is a flowchart showing an example of a method of measuring the scattering parameters of a test fixture with reflective terminations having different reflection coefficients at the second port.

FIG. 16 is a flow chart showing an example 700 of a method based on method 500 for measuring scattering parameters of a test fixture having a first port and a second port. Method 700 generates two sets of scattering parameters for test fixture 10 with the second port 40 of the test fixture terminated in respective reflective terminations having different reflection coefficients. Corresponding scattering parameters in the two sets of scattering parameters are then averaged to generate a single set of averaged scattering parameters. The averaged scattering parameters are more accurate than the scattering parameters in either of the sets of scattering parameters. In block 702, a first set of scattering parameters is generated for the test fixture using method 500, described above with reference to FIG. 12. In generating the first set of scattering parameters, block 504 of method 500 is performed with the second port of the test fixture terminated in a first reflective termination having a first reflection coefficient. In block 704, a second set of scattering parameters for the test fixture is generated using blocks 504, 506, 508, and 510 of method 500. In generating the second set of scattering parameters, block 504 method 500 is performed with the second port of the test fixture terminated in a second reflective termination having a second reflection coefficient, different from the first reflection coefficient. In block 706, corresponding scattering parameters are averaged between the first set of scattering parameters and the second set of scattering parameters to generate respective average scattering parameters.

In an example of method 700, one of the first reflective termination and the second reflective termination is a short circuit and the other of the first reflective termination and the second reflective termination is an open circuit.

Figure 17:
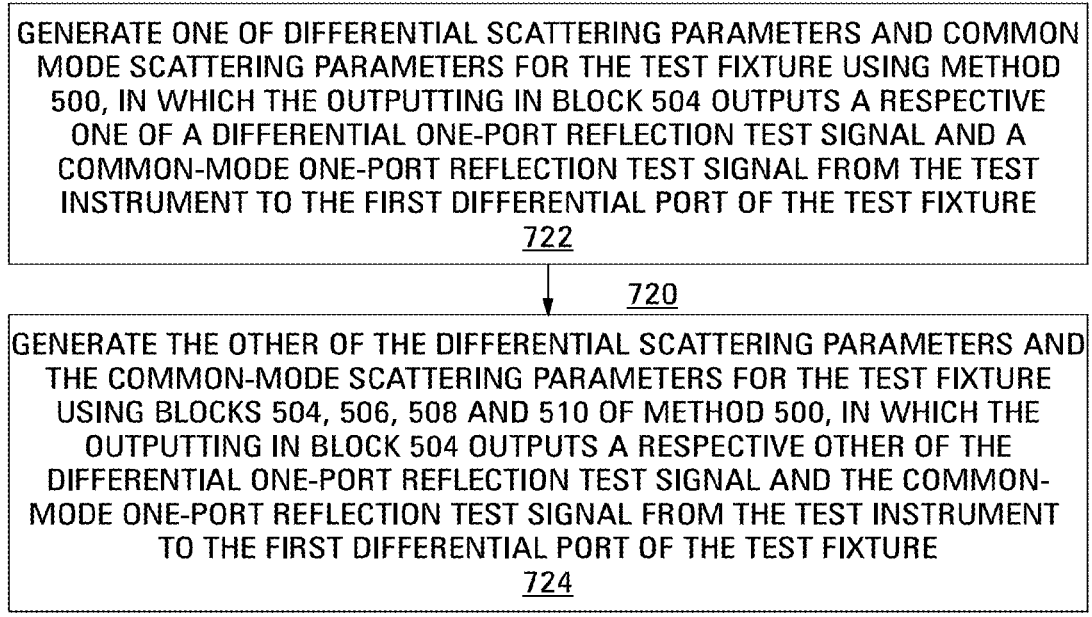
FIG. 17 is a flowchart showing an example of measuring the scattering parameters of a test fixture having differential ports.

FIG. 17 is a flowchart showing an example 720 of a method based on method 500, described above with reference to FIG. 12, for determining the scattering parameters of an embodiment of test fixture 10 in which the first port and the second port of the test fixture are differential ports. In block 722, one of differential scattering parameters and common-mode scattering parameters are generated for the test fixture using method 500. The outputting performed in block 504 of the instance of method 500 performed in block 722 outputs a respective one of a differential one-port reflection test signal and a common-mode one-port reflection test signal from the test instrument to the first differential port of the test fixture. In an example in which differential scattering parameters Sdd11, Sdd12, Sdd21, and Sdd22 are generated in block 722, the test instrument outputs a differential one-port reflection test signal when block 504 of method 500 is performed in block 722. In an example in which common-mode scattering parameters Scc11, Scc12, Scc21, and Scc22 are generated in block 722, the test instrument outputs a common-mode one-port reflection test signal when block 504 of method 500 is performed in block 722.

In block 724, the other of the differential scattering parameters and the common-mode scattering parameters for the test fixture are generated using blocks 504, 506, 508, and 510 of method 500. The outputting performed in block 504 performed in block 724 outputs a respective other of the differential one-port reflection test signal and the common-mode one-port reflection test signal from the test instrument to the first differential port of the test fixture. In an example in which differential scattering parameters Sdd11, Sdd12, Sdd21, and Sdd22 were generated in block 722, common-mode scattering parameters Scc11, Scc12, Scc21, and Scc22 are generated in block 724, and the test instrument outputs a common-mode one-port reflection test signal when block 504 is performed in block 724. In an example in which common-mode scattering parameters Scc11, Scc12, Scc21, and Scc22 were generated in block 722, differential scattering parameters Sdd11, Sdd12, Sdd21, and Sdd22 are generated in block 724, and the test instrument outputs a differential one-port reflection test signal when block 504 is performed in block 724.

Embodiments disclosed herein include:

A system to measure scattering parameters of a test fixture having a first port and a second port. The system comprises an input to receive a first time-gated measurement signal and a second time-gated measurement signal obtained by subjecting a one-port measurement signal to time gating, the one-port measurement signal obtained from the first port of the test fixture with the second port of the test fixture terminated in a reflective termination having a known reflection coefficient, the first time-gated measurement signal obtained using a first gating function temporally disposed about the first port, the second time-gated measurement signal obtained using a second gating function temporally disposed about the reflective termination; a first port return loss generator to generate from the first time-gated measurement signal a first port return loss for the test fixture; an insertion loss generator to generate from the second time-gated measurement signal and the reflection coefficient a two-way insertion loss, a first port reverse insertion loss, and a first port forward insertion loss for the test fixture; and a second port return loss generator to generate a second-port return loss for the test fixture from the first port return loss, the two-way insertion loss, the first port reverse insertion loss, the first port forward insertion loss, and the reflection coefficient.

The above-described system in which the first time-gated measurement signal is a frequency-domain signal; and the first port return loss generator comprises a conductor to output the first time-gated measurement signal as a first port return loss signal representing, as a first scattering parameter, the first port return loss of the test fixture.

The above-described system in which the second time-gated measurement signal is a time-domain signal; and the insertion loss generator comprises a time domain to frequency domain transform processor to transform the second time-gated measurement signal from the time domain to the frequency domain to generate a two-way insertion loss signal representing the two-way insertion loss of the test fixture, a divider to divide the two-way insertion loss signal by the reflection coefficient to generate a quotient, and a square root calculator to calculate the square root of the quotient to generate a first port reverse insertion loss signal representing, as a second scattering parameter, the first port reverse insertion loss of the test fixture. In some embodiments, the insertion loss generator additionally comprises a conductor to output the first port reverse insertion loss signal as a first port forward insertion loss signal representing, as a third scattering parameter, the first port forward insertion loss of the test fixture.

The above-described system in which the second time-gated measurement signal is a frequency-domain signal; and the insertion loss generator comprises a divider to divide the second time-gated measurement signal by the reflection coefficient of the termination to generate a quotient, and a square root calculator to calculate the square root of the quotient to provide a first port reverse insertion loss signal representing, as a second scattering parameter, the reverse insertion loss of the test fixture. In some embodiments, the insertion loss generator additionally comprises a conductor to output the first port reverse insertion loss signal as a first port forward insertion loss signal representing, as a third scattering parameter, the first port forward insertion loss of the test fixture.

The above-described system in which the first time-gated measurement signal and the second time-gated measurement signal are respective frequency-domain signals; and the second port return loss generator comprises an input to receive the first time-gated measurement signal representing the first port return loss, an input to receive the second time-gated measurement signal representing the two-way insertion loss, inputs to receive from the insertion loss generator a first port reverse insertion loss signal and a first port forward insertion loss signal representing the first port reverse insertion loss and the first port forward insertion loss, respectively, a first multiplier to multiply the first time-gated measurement signal, the first port forward insertion loss signal, and the reflection coefficient to generate a product, a first subtractor to subtract the first time-gated measurement signal from the second time-gated measurement signal to generate a first difference, a divider to divide the product by the first difference to generate a quotient, a second subtracter to subtract the quotient from unity to generate a second difference, and a second multiplier to multiply the second difference by the reflection coefficient to generate a second port return loss signal representing, a fourth scattering parameter, the second port return loss of the test fixture. In some embodiments, the second port return loss signal is a preliminary second port return loss signal; and the second port return loss generator additionally comprises a time domain to frequency domain transform processor to transform a third gating function signal representing a third gating function from the time domain to the frequency domain to generate a frequency-domain third gating function signal, and a convolution processor to subject the preliminary second port return loss signal and the frequency-domain third gating function signal to convolution to generate a final second port return loss signal representing the second port return loss of the test fixture.

The above-described system in which the test fixture is specified for use over a frequency range of interest having a maximum frequency; and the first port return loss processor, the insertion loss processor, and the second port return loss processor are configured to operate over a frequency range having a maximum frequency greater than the maximum frequency of the frequency range of interest.

The above-described system in which the one-port reflection measurement signal is a time-domain signal; the first gating function signal and the second time gating function signal are respective time-domain signals; the system additionally comprises a time gating processor to subject the one-port reflection measurement signal to time gating using the first gating function signal to generate the first time-gated measurement signal, and to subject the one-port reflection measurement system to time gating using the second gating function signal to generate the second time-gated measurement signal; and the time gating processor comprises a first time domain to frequency domain transform processor to transform the one-port reflection measurement signal from the time domain to the frequency domain to generate a frequency-domain one-port reflection measurement signal, a second time domain to frequency domain transform processor to transform the first gating function signal and the second gating function signal from the time domain to the frequency domain to generate a frequency-domain first gating function signal and a frequency-domain second gating function signal, respectively, and a convolution processor to subject the frequency-domain first gating function signal and the frequency-domain one-port reflection measurement signal to convolution to generate the first time-gated measurement signal as a frequency-domain signal, and to subject the frequency-domain second gating function signal and the frequency-domain one-port reflection measurement signal to convolution to generate the second time-gated measurement signal as a frequency-domain signal.

The above-described system in which the one-port reflection measurement is a frequency-domain signal; the first gating function signal and the second time gating function signal are respective time-domain signals; the system additionally comprises a time gating processor to subject the one-port reflection measurement signal to time gating using the first gating function signal to generate the first time-gated measurement signal, and to subject the one-port reflection measurement signal to time gating using the second gating function signal to generate the second time-gated measurement signal; and the time gating processor comprises a frequency domain to time domain transform processor to transform the one-port reflection measurement signal from the frequency domain to the time domain to generate a time-domain one-port reflection measurement signal, and a multiplier to multiply the time-domain one-port reflection measurement and the first gating function signal to generate the first time-gated measurement signal as a time-domain signal, and to multiply the time-domain one-port reflection measurement signal and the second gating function signal to generate the second time-gated measurement signal as a time-domain signal.

The above-described system, additionally comprising a time gating processor to subject the one-port reflection measurement signal to time gating using the first gating function to generate the first time-gated measurement signal, and to subject the one-port reflection measurement system to time gating using the second gating function to generate the second time-gated measurement signal; and a test instrument to output the one-port reflection test signal to the first port of the test fixture, and to receive the one-port reflection measurement signal from the first port of the test fixture.

Embodiments disclosed herein also include:

A method of measuring scattering parameters of a test fixture having a first port and a second port, the method comprising providing a test instrument; with the second port of the test fixture terminated in a reflective termination having a known reflection coefficient, outputting a one-port reflection test signal from the test instrument to the first port of the test fixture, and receiving at the test instrument a one-port reflection measurement signal from the first port of the test fixture; subjecting the one-port reflection measurement signal to first time gating to generate a first time-gated measurement signal, the first time gating using a first gating function temporally disposed about the first port; subjecting the one-port reflection measurement signal to second time gating to generate a second time-gated measurement signal, the second time gating using a second gating function temporally disposed about the termination; and deriving the scattering parameters of the test fixture from the first time-gated measurement signal and the second time-gated measurement signal.

The above-described method in which the second time-gated measurement signal is a frequency-domain signal; and the deriving the scattering parameters comprises deriving a first port reverse insertion loss signal representing, as a second scattering parameter, a reverse insertion loss at the first port of the test fixture, the deriving the first port reverse insertion loss signal comprising dividing the second time-gated measurement signal by the reflection coefficient of the termination to generate a quotient, and calculating the square root of the quotient to provide the first port reverse insertion loss signal. In some embodiments, the deriving the scattering parameters additionally comprises outputting the first port reverse insertion loss signal as a first port forward insertion loss signal representing, as a third scattering parameter, a forward insertion loss at the first port of the test fixture.

The above-described method in which the test fixture is specified for use over a frequency range of interest having a maximum frequency; and the deriving is performed over a frequency range having a maximum frequency greater than the maximum frequency of the frequency range of interest.

The above-described method in which the test instrument generates the one-port reflection measurement signal as a time-domain signal; the first gating function and the second time gating function are represented by respective time-domain signals; the subjecting the one-port reflection measurement signal to first time gating comprises multiplying the one-port reflection measurement signal and the first gating function signal to generate the first time-gated measurement signal as a time-domain signal; and the subjecting the one-port reflection measurement signal to second time gating comprises multiplying the one-port reflection measurement signal and the second time-domain gating function signal to generate the second time-gated measurement signal as a time-domain signal.

The above-described method in which the test instrument generates the one-port reflection measurement signal as a frequency-domain signal; the first gating function and the second time gating function are represented by respective time-domain signals; the method additionally comprises transforming the first gating function signal and the second gating function signal from the time domain to the frequency domain to generate a frequency-domain first gating function signal and a frequency-domain second gating function signal, respectively; the subjecting the one-port reflection measurement signal to first time gating comprises subjecting the frequency-domain first gating function signal and the one-port reflection measurement signal to convolution to generate the first time-gated measurement signal as a frequency-domain signal; and the subjecting the one-port reflection measurement signal to second time gating comprises subjecting the frequency-domain second gating function signal and the one-port reflection measurement signal to convolution to generate the second time-gated measurement signal as a frequency-domain signal.

The above-described method in which the test instrument generates the one-port reflection measurement signal as a time-domain signal; the first gating function and the second time gating function are represented by respective time-domain signals; the method additionally comprises transforming the one-port reflection measurement signal from the time domain to the frequency domain to generate a frequency-domain one-port reflection measurement signal, and transforming the first gating function signal and the second gating function signal from the time domain to the frequency domain to generate a frequency-domain first gating function signal and a frequency-domain second gating function signal, respectively; the subjecting the one-port reflection measurement signal to first time gating comprises subjecting the frequency-domain first gating function signal and the frequency-domain one-port reflection measurement signal to convolution to generate the first time-gated measurement signal as a frequency-domain signal; and the subjecting the one-port reflection measurement signal to second time gating comprises subjecting the frequency-domain second gating function signal and the frequency-domain one-port reflection measurement signal to convolution to generate the second time-gated measurement signal as a frequency-domain signal.

The above-described method in which the test instrument generates the one-port reflection measurement signal as a frequency-domain signal; the first gating function and the second time gating function are represented by respective time-domain signals; the method additionally comprises transforming the one-port reflection measurement signal from the frequency domain to the time domain to generate a time-domain one-port reflection measurement signal; the subjecting the one-port reflection measurement signal to first time gating comprises multiplying the time-domain one-port reflection measurement signal and the first gating function signal to generate the first time-gated measurement signal as a time-domain signal; and the subjecting the one-port reflection measurement signal to second time gating comprises multiplying the time-domain one-port reflection measurement signal and the second gating function signal to generate the second time-gated measurement signal as a time-domain signal.

The above-described method in which the first port and the second port are single-ended ports; and the deriving derives single-ended scattering parameters S11, S12, S21, and S22 for the test fixture from the first time-gated measurement signal and the second time-gated measurement signal.

A method of measuring scattering parameters of a test fixture having a first port and a second port. The method comprises generating a first set of scattering parameters for the test fixture using the above-described method, in which the outputting and the receiving are performed with the second port of the test fixture terminated in a first reflective termination having a first reflection coefficient; generating a second set of scattering parameters for the test fixture using the outputting, the receiving, the subjecting, the subjecting, and the deriving of the above-described method, in which the outputting and the receiving are performed with the second port of the test fixture terminated in a second reflective termination having a second reflection coefficient, different from the first reflection coefficient; and averaging corresponding scattering parameters between the first set of scattering parameters and the second set of scattering parameters to generate respective average scattering parameters. In some embodiments, one of the first reflective termination and the second reflective termination is a short circuit and the other of the first reflective termination and the second reflective termination is an open circuit.

This disclosure describes the invention in detail using illustrative embodiments. However, the invention defined by the appended claims is not limited to the precise embodiments described.

We claim:

1. A system to measure scattering parameters of a test fixture having a first port and a second port, the system comprising:
    an input to receive a first time-gated measurement signal and a second time-gated measurement signal obtained by subjecting a one-port measurement signal to time gating, the one-port measurement signal obtained from the first port of the test fixture with the second port of the test fixture terminated in a reflective termination having a known reflection coefficient, the first time-gated measurement signal obtained using a first gating function temporally disposed about the first port, the second time-gated measurement signal obtained using a second gating function temporally disposed about the reflective termination;
    a first port return loss generator to generate from the first time-gated measurement signal a first port return loss for the test fixture;
    an insertion loss generator to generate from the second time-gated measurement signal and the reflection coefficient a two-way insertion loss, a first port reverse insertion loss, and a first port forward insertion loss for the test fixture; and
    a second port return loss generator to generate a second-port return loss for the test fixture from the first port return loss, the two-way insertion loss, the first port reverse insertion loss, the first port forward insertion loss, and the reflection coefficient.

2. The system of claim 1, in which:
    the first time-gated measurement signal is a time-domain signal; and
    the first port return loss generator comprises a time domain to frequency domain transform processor to transform the first time-gated measurement signal from the time domain to the frequency domain to provide a first port return loss signal representing, as a first scattering parameter, the first port return loss of the test fixture.

3. The system of claim 1, in which:
    the second time-gated measurement signal is a time-domain signal; and
    the insertion loss generator comprises:
        a time domain to frequency domain transform processor to transform the second time-gated measurement signal from the time domain to the frequency domain to generate a two-way insertion loss signal representing the two-way insertion loss of the test fixture,
        a divider to divide the two-way insertion loss signal by the reflection coefficient to generate a quotient, and
        a square root calculator to calculate the square root of the quotient to generate a first port reverse insertion loss signal representing, as a second scattering parameter, the first port reverse insertion loss of the test fixture.

4. The system of claim 1, in which:
    the first time-gated measurement signal and the second time-gated signals are respective time-domain signals; and
    the second port return loss generator comprises:
        an input to receive from the first port return loss generator a first port return loss signal representing the first port return loss,
        inputs to receive from the insertion loss generator a two-way insertion loss signal, a first port reverse insertion loss signal and a first port forward insertion loss signal representing the two way insertion loss, the first port reverse insertion loss and the first port forward insertion loss, respectively, a first multiplier to multiply the first port reverse insertion loss signal, the first port forward insertion loss signal, and the reflection coefficient to generate a product, a first subtracter to subtract the first port return loss signal from the two-way insertion loss signal to generate a first difference, a divider to divide the product by the first difference to generate a quotient, a second subtracter to subtract the quotient from unity to generate a second difference, and a second multiplier to multiply the second difference by the reflection coefficient to generate a second port return loss signal representing, as a fourth scattering parameter, the second port return loss of the test fixture.

5. The system of claim 4, in which:

the second port return loss signal is a preliminary second port return loss signal; and the second port return loss generator additionally comprises:

a frequency domain to time domain transform processor to transform the preliminary second port return loss signal from the frequency domain to the time domain to generate a time-domain return loss signal, a time gating processor to subject the time-domain return loss signal to time gating with a third gating function to generate a time-gated return loss signal, the third gating function temporally disposed about the termination, and a time domain to frequency domain transform processor to transform the time-gated return loss signal from the time domain to the frequency domain to generate a final second port return loss signal representing the second port return loss of the test fixture.

6. The system of claim 1, in which:

the one-port reflection measurement signal is a time-domain signal;

the first gating function and the second time gating function are represented by respective time-domain signals;

the system additionally comprises a time gating processor to subject the one-port reflection measurement signal to time gating using the first gating function to generate the first time-gated measurement signal, and to subject the one-port reflection measurement system to time gating using the second gating function to generate the second time-gated measurement signal, and the time gating processor comprises a multiplier to multiply the one-port reflection measurement signal and the first gating function signal to generate the first time-gated measurement signal as a time-domain signal and to multiply the one-port reflection measurement signal and the second time-domain gating function signal to generate the second time-gated measurement signal as a time-domain signal.

7. The system of claim 1, in which:

the one-port reflection measurement signal is a frequency-domain signal;

the first gating function and the second time gating function are represented by respective time-domain signals;

the system additionally comprises a time gating processor to subject the one-port reflection measurement signal to time gating using the first gating function to generate the first time-gated measurement signal, and to subject the one-port reflection measurement system to time gating using the second gating function to generate the second time-gated measurement signal, and the time gating processor comprises:

a time domain to frequency domain transform processor to transform the first gating function signal and the second gating function signal from the time domain to the frequency domain to generate a frequency-domain first gating function signal and a frequency-domain second gating function signal, respectively, and a convolution processor to subject the frequency-domain first gating function signal and the one-port reflection measurement signal to convolution to generate the first time-gated measurement signal as a frequency-domain signal, and to subject the frequency-domain second gating function signal and the one-port reflection measurement signal to convolution generate the second time-gated measurement signal as a frequency-domain signal.

8. The system of claim 1, in which:

the first port and the second port of the test fixture are differential ports;

the system additionally comprises:

a test instrument to output the one-port reflection test signal to the first port of the test fixture, and to receive the one-port reflection measurement signal from the first port of the test fixture as respective differential signals, and a time gating processor to subject the one-port reflection measurement signal to time gating using the first gating function to generate the first time-gated measurement signal, and to subject the one-port reflection measurement system to time gating using the second gating function to generate the second time-gated measurement signal, the time gating comprising:

first time gating using the first gating function to generate a first differential time-gated measurement signal; and second time gating using the second gating function to generate a second differential time-gated measurement signal, the first port return loss generator, the insertion loss generator and the second port return loss generator are to generate differential scattering parameters Sdd11, Sdd12, Sdd21, Sdd22 for the test fixture from the first differential time-gated measurement signal and the second differential time-gated measurement signal;

the test instrument is additionally to output a common-mode one-port reflection test signal to the first port of the test fixture with the second port of the test fixture terminated in the reflective termination, and is additionally to receive a common-mode one-port reflection measurement signal from the first port of the test fixture;

the gating processor is additionally to subject the common-mode one-port reflection measurement signal to time gating, the time gating comprising:

first time gating using the first gating function to generate a first common-mode time-gated measurement signal, and second time gating using the second gating function to generate a second common-mode time-gated measurement signal; and the first port return loss generator, the insertion loss generator and the second port return loss generator are additionally to generate common-mode scattering parameters Scc11, Scc12, Scc21, Scc22 of the test fixture from the first common-mode time-gated measurement signal and the second common-mode time-gated measurement signal.

9. A method of measuring scattering parameters of a test fixture having a first port and a second port, the method comprising:
providing a test instrument;
with the second port of the test fixture terminated in a reflective termination having a known reflection coefficient, outputting a one-port reflection test signal from the test instrument to the first port of the test fixture, and receiving at the test instrument a one-port reflection measurement signal from the first port of the test fixture;
subjecting the one-port reflection measurement signal to first time gating to generate a first time-gated measurement signal, the first time gating using a first gating function temporally disposed about the first port;
subjecting the one-port reflection measurement signal to second time gating to generate a second time-gated measurement signal, the second time gating using a second gating function temporally disposed about the termination; and
deriving the scattering parameters of the test fixture from the first time-gated measurement signal and the second time-gated measurement signal.

10. The method of claim 9, in which:
the first time-gated measurement signal is a time-domain signal; and
the deriving comprises transforming the first time-gated measurement signal from the time domain to the frequency domain to provide a first port return loss signal representing, as a first scattering parameter, a return loss at the first port of the test fixture.

11. The method of claim 9, in which:
the first time-gated measurement signal is a frequency-domain signal; and
the deriving comprises outputting the first time-gated measurement signal to provide a first port return loss signal representing, as a first scattering parameter, a return loss at the first port of the test fixture.

12. The method of claim 9, in which:
the second time-gated measurement signal is a time-domain signal; and
the deriving the scattering parameters comprises deriving a first port reverse insertion loss signal representing, as a second scattering parameter, a reverse insertion loss at the first port of the test fixture, the deriving the first port reverse insertion loss signal comprising:
transforming the second time-gated measurement signal from the time domain to the frequency domain to generate a two-way insertion loss signal representing a two-way insertion loss of the test fixture,
dividing the two-way insertion loss signal by the reflection coefficient of the termination to generate a quotient, and
calculating the square root of the quotient to generate the first port reverse insertion loss signal.

13. The method of claim 12, in which the deriving the scattering parameters additionally comprises outputting the first port reverse insertion loss signal as a first port forward insertion loss signal representing, as a third scattering parameter, a forward insertion loss at the first port of the test fixture.

14. The method of claim 9, in which:
the first time-gated measurement signal and the second time-gated measurement signal are respective time-domain signals; and
the deriving comprises:
transforming the first time-gated measurement signal from the time domain to the frequency domain to generate a first port return loss signal representing a return loss at the first port of the test fixture,
transforming the second time-gated measurement signal from the time domain to the frequency domain to generate a two-way insertion loss signal representing a two-way insertion loss of the test fixture,
dividing the two-way insertion loss signal by the reflection coefficient of the termination to generate a first quotient,
calculating the square root of the first quotient to generate a first port reverse insertion loss signal representing a reverse insertion loss at the first port of the test fixture, and a first port forward insertion loss signal representing a forward insertion loss at the first port of the test fixture,
multiplying the first port reverse insertion loss signal, the first port forward insertion loss signal, and the reflection coefficient to generate a product,
subtracting the first port return loss signal from the two-way insertion loss signal to generate a first difference,
dividing the product by the first difference to generate a second quotient,
subtracting the second quotient from unity to generate a second difference, and
multiplying the second difference by the reflection coefficient to generate a second port return loss signal representing, as a fourth scattering parameter, a return loss at the second port of the test fixture.

15. The method of claim 14, in which:
the second port return loss signal is a preliminary second port return loss signal; and
the deriving additionally comprises:
transforming the preliminary second port return loss signal from the frequency domain to the time domain to generate a time-domain return loss signal,
subjecting the time-domain return loss signal to time gating with a third gating function to generate a time-gated return loss signal, the third gating function temporally disposed about the second port, and
transforming the time-gated return loss signal from the time domain to the frequency domain to generate a final second port return loss signal representing the return loss at the second port of the test fixture.

16. The method of claim 9, in which:
the first time-gated measurement signal and the second time-gated measurement signal are respective frequency-domain signals; and
the deriving additionally comprises:
dividing the second time-gated measurement signal by the reflection coefficient of the termination to generate a first quotient, and
calculating the square root of the first quotient to generate a first port reverse insertion loss signal representing the reverse insertion loss at the first port of the text fixture, and a first port forward insertion loss signal representing the forward insertion loss at the first port of the test fixture,
multiplying the first port reverse insertion loss signal, the first port forward insertion loss signal, and the reflection coefficient to generate a product;

subtracting the first time-gated measurement signal from the second time-gated measurement signal to generate a first difference;

dividing the product by the first difference to generate a second quotient;

subtracting the second quotient from unity to generate a second difference; and multiplying the second difference by the reflection coefficient to generate a second port return loss signal representing, a fourth scattering parameter, a return loss at the second port of the test fixture.

17. The method of claim 16, in which:

the second port return loss signal is a preliminary second port return loss signal; and the deriving additionally comprises:

providing a third gating function signal representing a third gating function, temporally disposed about the termination, transforming the third gating function signal from the time domain to the frequency domain to generate a frequency-domain third gating function signal, and subjecting the preliminary second port return loss signal and the frequency-domain third gating function signal to convolution to generate a final second port return loss signal that represents the return loss at the second port of the test fixture.

18. The method of claim 9, in which the reflective termination is one of an open circuit and a short circuit.

19. A method of measuring scattering parameters of a test fixture having a first port and a second port, the method comprising:

generating a first set of scattering parameters for the test fixture using the method of claim 9, in which the outputting and the receiving are performed with the second port of the test fixture terminated in a first reflective termination having a first reflection coefficient;

generating a second set of scattering parameters for the test fixture using the outputting, the receiving, the subjecting, the subjecting, and the deriving of the method of claim 9, in which the outputting and the receiving are performed with the second port of the test fixture terminated in a second reflective termination having a second reflection coefficient, different from the first reflection coefficient; and averaging corresponding scattering parameters between the first set of scattering parameters and the second set of scattering parameters to generate respective average scattering parameters.

20. A method of measuring scattering parameters of a test fixture having a first differential port and a second differential port, the method comprising:

generating one of differential scattering parameters and common-mode scattering parameters for the test fixture using the method of claim 9, in which the outputting comprises outputting a respective one of a differential one-port reflection test signal and a common-mode one-port reflection test signal from the test instrument to the first differential port of the test fixture; and generating the other of differential scattering parameters and common-mode scattering parameters for the test fixture using the outputting, the receiving, the subjecting, the subjecting, and the deriving of the method of claim 9, in which the outputting comprises outputting a respective other of a differential one-port reflection test signal and a common-mode one-port reflection test signal from the test instrument to the first differential port of the test fixture.

* * * * *